(12) United States Patent
Fowler

(10) Patent No.: US 9,056,340 B2
(45) Date of Patent: Jun. 16, 2015

(54) BIOREMEDIATION SYSTEMS, COMPOSITIONS, AND METHODS

(75) Inventor: Troy John Fowler, Beaverton, OR (US)

(73) Assignee: Bioremediation Specialists L.L.C., Beaverton, OR (US)

( * ) Notice: Subject to any disclaimer, the term of this patent is extended or adjusted under 35 U.S.C. 154(b) by 0 days.

(21) Appl. No.: 13/565,584

(22) Filed: Aug. 2, 2012

(65) Prior Publication Data

US 2013/0260441 A1 Oct. 3, 2013

Related U.S. Application Data

(63) Continuation-in-part of application No. 13/436,532, filed on Mar. 30, 2012, now abandoned.

(51) Int. Cl.
| | | |
|---|---|---|
| *C12N 1/00* | (2006.01) | |
| *B09C 1/08* | (2006.01) | |
| *C12N 1/20* | (2006.01) | |
| *C02F 1/42* | (2006.01) | |
| *C02F 3/28* | (2006.01) | |
| *C02F 103/06* | (2006.01) | |
| *C02F 101/20* | (2006.01) | |
| *C02F 101/30* | (2006.01) | |
| *C02F 101/32* | (2006.01) | |

(52) U.S. Cl.
CPC ... *B09C 1/08* (2013.01); *C12N 1/20* (2013.01); *C02F 2103/06* (2013.01); *C02F 1/42* (2013.01); *C02F 3/28* (2013.01); *C02F 2001/425* (2013.01); *C02F 2101/20* (2013.01); *C02F 2101/30* (2013.01); *C02F 2101/32* (2013.01); *C02F 2305/04* (2013.01); *C02F 2305/06* (2013.01)

(58) Field of Classification Search
None
See application file for complete search history.

(56) References Cited

U.S. PATENT DOCUMENTS

| | | | |
|---|---|---|---|
| 5,059,252 A | 10/1991 | Renfro, Jr. | |
| 5,158,595 A | 10/1992 | Stillman | |
| 5,160,488 A | 11/1992 | Stillman | |
| 5,340,376 A | 8/1994 | Cunningham | |

(Continued)

FOREIGN PATENT DOCUMENTS

WO  WO2008/117301 A1  10/2008

OTHER PUBLICATIONS

Mulligan et al., Eng, Geo., 60:371-380 (2001).*

(Continued)

*Primary Examiner* — Blaine Lankford
*Assistant Examiner* — Thomas J Visone
(74) *Attorney, Agent, or Firm* — DASCENZO Intellectual Property Law, P.C.

(57) ABSTRACT

Systems, compositions, and methods for the bioremediation of a contaminant contained within a contaminated region. The systems, compositions, and methods may include supplying a first bioremediation formulation that includes an ion exchange resin to a first treatment zone that is associated with the contaminated region. The systems, compositions, and methods further may include supplying a second bioremediation formulation that includes a high-mobility oxidant, a low-mobility oxidant, and a nutrient material to a second treatment zone that is associated with the contaminated region. The systems, compositions, and methods also may include a kit of bioremediation formulations that includes the first bioremediation formulation and the second bioremediation formulation and is to be utilized during the bioremediation of the contaminated region.

15 Claims, 4 Drawing Sheets

(56) References Cited

U.S. PATENT DOCUMENTS

| | | | |
|---|---|---|---|
| 5,560,737 | A | 10/1996 | Schuring et al. |
| 5,582,627 | A | 12/1996 | Yamashita |
| 5,753,122 | A | 5/1998 | Taylor et al. |
| 5,766,929 | A | 6/1998 | Orolin et al. |
| 5,922,204 | A | 7/1999 | Hunter et al. |
| 6,020,185 | A * | 2/2000 | Hince et al. ............ 435/262 |
| 6,171,844 | B1 | 1/2001 | Numata et al. |
| 6,537,797 | B1 | 3/2003 | Picardal et al. |
| 6,562,235 | B1 | 5/2003 | Newell et al. |
| 6,841,515 | B2 | 1/2005 | Burnham |
| 7,022,234 | B2 | 4/2006 | Shaffer et al. |
| 7,138,060 | B2 | 11/2006 | Cuthbertson |
| 7,413,890 | B1 | 8/2008 | Hince et al. |
| 7,425,267 | B2 | 9/2008 | Sumino et al. |
| 2004/0007524 | A1* | 1/2004 | Noland et al. ............ 210/610 |
| 2005/0239189 | A1 | 10/2005 | Schaffner |
| 2005/0260739 | A1 | 11/2005 | Rosen et al. |
| 2006/0166348 | A1 | 7/2006 | Gerritse et al. |
| 2008/0026944 | A1 | 1/2008 | Alfrey et al. |
| 2008/0227179 | A1 | 9/2008 | Smith et al. |
| 2008/0296223 | A1 | 12/2008 | Hiromoto |
| 2010/0227381 | A1 | 9/2010 | Hoag et al. |

OTHER PUBLICATIONS

Berdugo-Clavijo, Carolina, et al. Methanogenic Biodegradation of Two-Ringed Polycyclic Aromatic Hydrocarbons; *Federation of European Microbiological Societies, Microbiology Ecology Journal*, vol. 80, Issue 1, pp. 1-10 (2012).

Ekiel, Irena, et al. Acetate and Co2 Assimilation by Methanothrix Concilii; *Journal of Bacteriology*, vol. 162, No. 3, pp. 905-908 (1985).

Heider, Johann, et al. Anaerobic Metabolism of Aromatic Compounds; *European Journal of Biochemistry*, vol. 243, Issue 3, pp. 577-596 (1997).

Katou, Hidetaka, et al. Anion Adsorption and Transport in an Unsaturated High-Humic Andosol; *19th World Congress of Soil Science, Soil Solutions for a Changing World*, Aug. 1-6, 2010, Brisbane, Australia.

Kleemann, Rita, et al. Anaerobic Naphthalene Degradation by Grampositive, Iron-reducing Bacteria; *Federation of European Microbiological Societies, Microbiology Ecology Journal*, vol. 78, Issue 3, pp. 488-496 (2011).

Marques, Silvia, et al. Transcriptional Control of the *Pseudomonas putida* TOL Plasmid Catabolic Pathways; *Molecular Microbiology*, vol. 9, Issue 5, pp. 923-929 (1993).

Mortimer, Robert J.G. et al. Evidence for Suboxic Nitrification in Recent Marine Sediments; *Marine Ecology Progress Series*, vol. 236, pp. 31-35 (2002).

Nam, I.-H, et al. A Novel Catabolic Activity of *Pseudomonas veronii* in Biotransformation of Pentachlorophenol; *Applied Microbiology and Biotechnology*, vol. 62, pp. 284-290 (2003).

O'Mahony, Mark, et al. The Use of Ozone in the Remediation of Polycyclic Aromatic Hydrocarbon Contaminated Soil; *Chemosphere*, vol. 63, pp. 307-314 (2006).

Russell, James B., et al. The Effects of Fermentation Acids on Bacterial Growth; *Advances in Microbial Physiology*, vol. 39, pp. 206-229 (1998).

Rothermich, Mary M., Hayes, et al. Anaerobic, Sulfate-Dependent Degradation of Polycyclic Aromatic Hydrocarbons in Petroleum-Contaminated Harbor Sediment; *Environmental Science and Technology*, vol. 36, pp. 4811-4817 (2002).

Soberon-Chavez, Gloria, et al. Production of Rhamnolipids by *Pseudomonas aeruginosa*; *Applied Microbiology and Biotechnology*, vol. 68, pp. 718-725 (2005).

Straub, K.L., et al. Anaerobic, Nitrate-Dependent Microbial Oxidation of Ferrous Iron; *Applied and Environmental Microbiology*, vol. 62, Issue 4, pp. 1458-1460 (1996).

Yen, Kwang-Mu et al. Cloning and Characterization of a *Pseudomonas mendocina* KR1 Gene Cluster Encoding Toluene-4-Monooxygenase; *Journal of Bacteriology*, vol. 173, No. 17, pp. 5315-5327.

Website screen capture from www.pseudomonas.com; *Pseudomonas aeruginosa PAO1 Pathway: Denitrification Pathway*. Accessed Apr. 2, 2012.

Material Safety Data Sheet for CONDOR Land Reclaimer from Earth Science Products, dated Jan. 20, 2011.

Product description for CONDOR LR—Land Reclaimer from earthscienceproducts.com, accessed Aug. 2, 2012.

Condor Technical Notes from earthscienceproducts.com, accessed Aug. 2, 2012.

Notice to Engineers regarding soil testing from earthscienceproducts.com, accessed Aug. 2, 2012.

Cunningham, Jeffrey A., Enhanced In Situ Bioremediation of BTEX-Contaminated Groundwater by Combined Injection of Nitrate and Sulfate; *Environmental Science & Technology*, 2001 vol. 35, No. 8, 1663-1670.

Kolhatkar, Ravi, et al., *Enhanced Bioremediation Using Sulfate and/or Nitrate*; Group Environmental Management Remediation Management Technology Meeting, Warrenville, Jan. 22, 2004.

Tang, Yinjie J., et al., Controlled Release of Nitrate and Sulfate to Enhance Anaerobic Bioremediation of Phenanthrene in Marine Sediments; *Environmental Science & Technology*, 2005 vol. 39, No. 9, 3368-3373.

\* cited by examiner

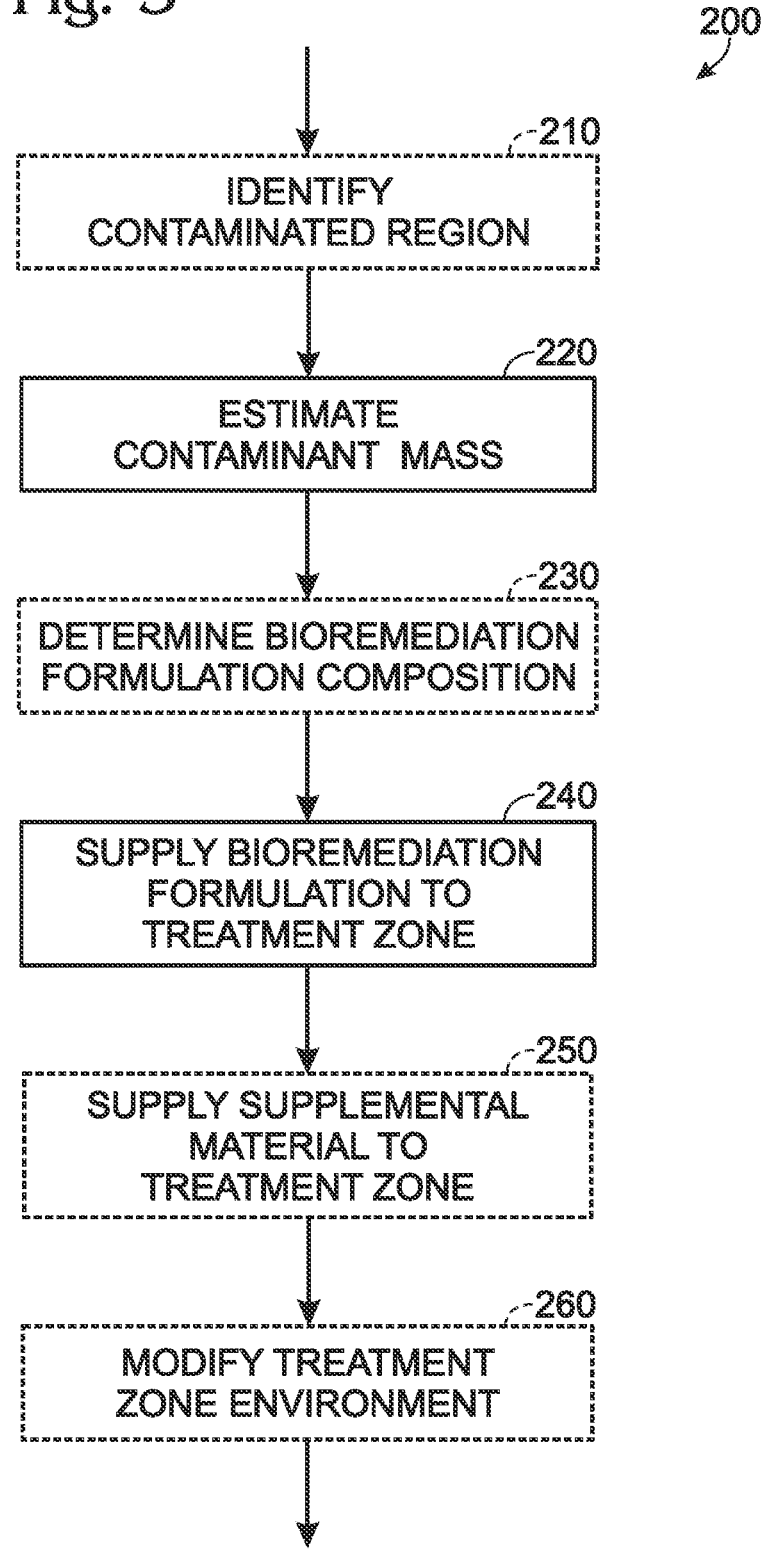

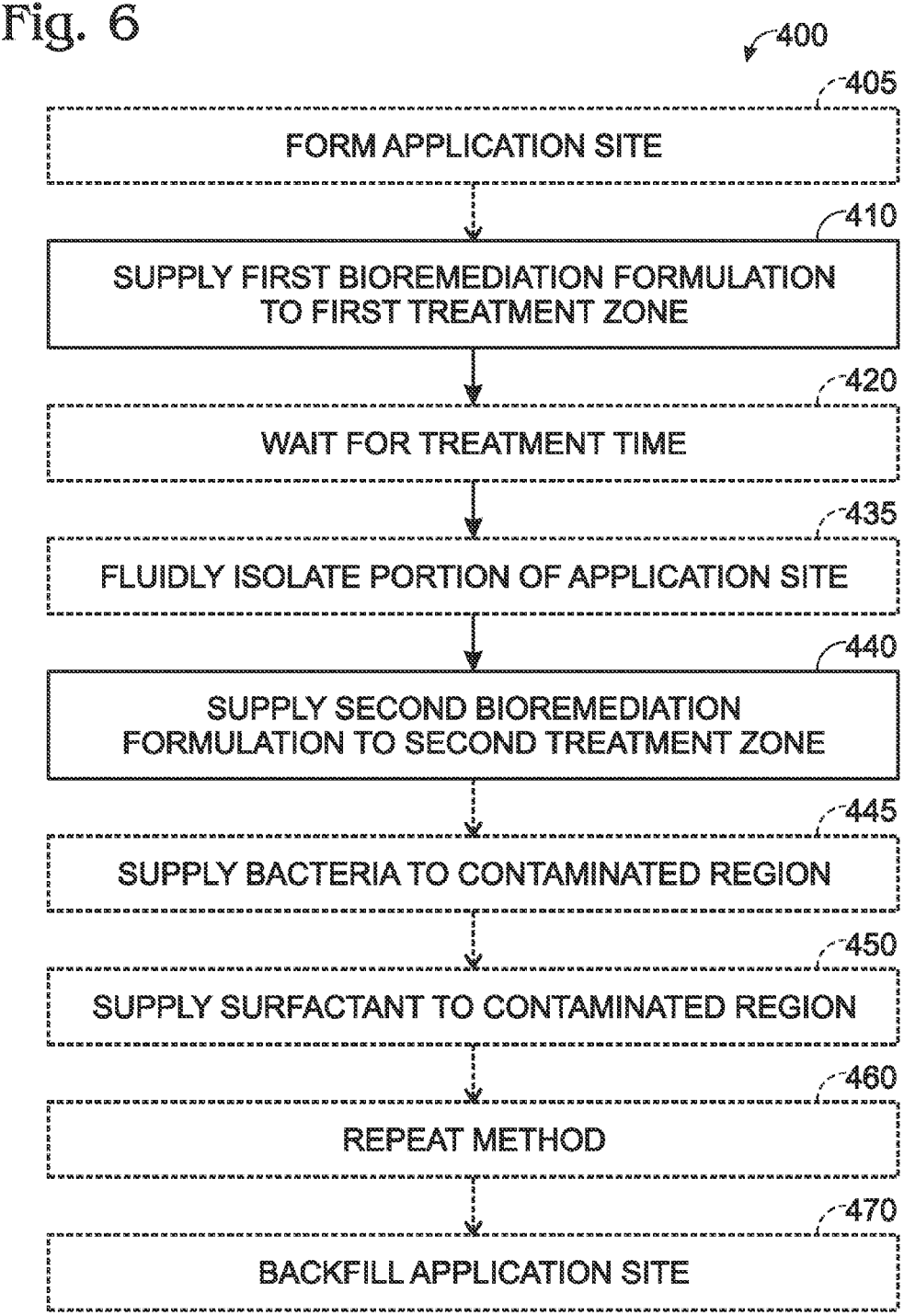

BIOREMEDIATION SYSTEMS, COMPOSITIONS, AND METHODS

RELATED APPLICATION

This application is a continuation-in-part of and claims priority to U.S. patent application Ser. No. 13/436,532, which was filed Mar. 30, 2012, the complete disclosure of which is incorporated herein by reference.

FIELD

The present disclosure is directed to systems, compositions, and methods for bioremediation of a contaminated region.

BACKGROUND

The natural environment, including water and/or soil, may become contaminated with contaminants, illustrative, non-exclusive examples of which include hydrocarbons, organic solvents, pesticides, herbicides, metals, partially halogenated solvents, and partially halogenated organics. These contaminants may be detrimental to a natural ecosystem that may interact with a contaminated region, or contaminated material, and/or may pose health hazards for humans, wildlife, the environment, ecosystems, and/or animals. Microorganisms, such as bacteria and fungi, may consume a portion of these contaminants as part of their natural respiratory processes. This consumption may decompose or degrade the contaminants into less harmful and/or benign respiration products, decreasing contaminant concentration within, or cleaning, the contaminated region, and may take place using aerobic and/or anaerobic reaction pathways. In aerobic respiration, molecular oxygen serves as the ultimate electron acceptor, or oxidant, for the respiratory process, while in anaerobic respiration, another chemical compound serves as the ultimate electron acceptor, or oxidant, for the respiratory process.

Bioremediation is the targeted and deliberate use of these biological, or respiratory, processes to degrade, consume, break down, transform, metabolize, and/or remove contaminants from a treatment zone that is associated with a contaminated region and may be performed both in situ and/or ex situ. In situ bioremediation includes treating the contaminated material without removal from its current, existing, or natural location, while ex situ bioremediation includes removal of the contaminated material from its current, existing, or natural location for treatment on the contaminated site (such as in land farming) or at a different site. Bioremediation processes that include the introduction of reactants for the respiration process, such as oxidants and/or nutrients, into the treatment zone to enhance, assist, augment, stimulate, and/or promote the growth of native microorganisms that are already present within the contaminated region are termed bio-stimulation processes, while bioremediation processes that include the introduction of non-native microorganisms into the treatment zone, with or without the introduction of oxidants and/or nutrients, are termed bio-augmentation processes.

For bioremediation to occur, a contaminated region must include a microbial population that is adapted to metabolize a contaminant, as well as an energy source, a carbon source, an electron acceptor (or oxidant), nutrients, and suitable environmental conditions. The microbial population may include native microbes and/or may include specialized microbes that may be added to the treatment zone during a bio-augmentation process. The contaminant is typically utilized by the microbial population as both the energy source and the carbon source, providing the mechanism by which the bioremediation processes may decrease a contaminant concentration within the treatment zone.

Once a suitable microbial population is present within the treatment zone, bio-stimulation processes may be utilized to increase a rate of contaminant consumption by the microbial population, such as by providing a source of oxidants and/or nutrients and/or by providing an environment that is more suitable for microbial growth. Illustrative, non-exclusive examples of environmental conditions that may impact microbial growth may include the temperature, pH, salinity, pressure, contaminant concentration, and/or an inhibitor concentration within the treatment zone.

SUMMARY

The present disclosure is directed to systems, compositions, and methods for the bioremediation of a contaminant contained within a contaminated region. The systems, compositions, and methods may include supplying a first bioremediation formulation that includes an ion exchange resin to a first treatment zone that is associated with the contaminated region. The systems, compositions, and methods further may include supplying a second bioremediation formulation that includes a high-mobility oxidant, a low-mobility oxidant, and a nutrient material to a second treatment zone that is associated with the contaminated region. The systems, compositions, and methods also may include a kit of bioremediation formulations that includes the first bioremediation formulation and the second bioremediation formulation and that is to be utilized during the bioremediation of the contaminated region.

These bioremediation formulations are configured to function cooperatively to reduce a concentration of the contaminant within the contaminated region and to provide at least a portion of the oxidants and nutrients that are consumed by a native microbe population during anaerobic respiration to promote the anaerobic oxidative bioremediation of the contaminant. In some embodiments, the ion exchange resin may include a cationic ion exchange resin. In some embodiments, the high-mobility oxidant may include any suitable chemical compound that may be highly mobile within the second treatment zone. In some embodiments, the low-mobility oxidant may include any suitable chemical compound that may be less mobile within the second treatment zone when compared to the high-mobility oxidant. In some embodiments, the high-mobility oxidant includes at least one nitrate salt. In some embodiments, the low-mobility oxidant includes at least one sulfate salt. In some embodiments, the nutrient material includes at least one complex sugar. In some embodiments, the nutrient material includes brewer's yeast. In some embodiments, the second bioremediation formulation also may include a mid-mobility oxidant, which may be more mobile than the low-mobility oxidant but less mobile than the high-mobility oxidant. In some embodiments, the mid-mobility oxidant may include a sulfate salt. In some embodiments, the second bioremediation formulation also may include at least a first phosphate salt. In some embodiments, the contaminated region may include at least one of a soil sample and a subsurface region.

BRIEF DESCRIPTION OF THE DRAWINGS

FIG. 5 is a flowchart depicting illustrative, non-exclusive examples of methods according to the present disclosure of supplying an oxidant and nutrients to a native microbe population.

FIG. 6 is a flowchart depicting illustrative, non-exclusive examples of methods according to the present disclosure of decreasing a concentration of a contaminant that is contained within a contaminated region.

DETAILED DESCRIPTION

Figure 1:
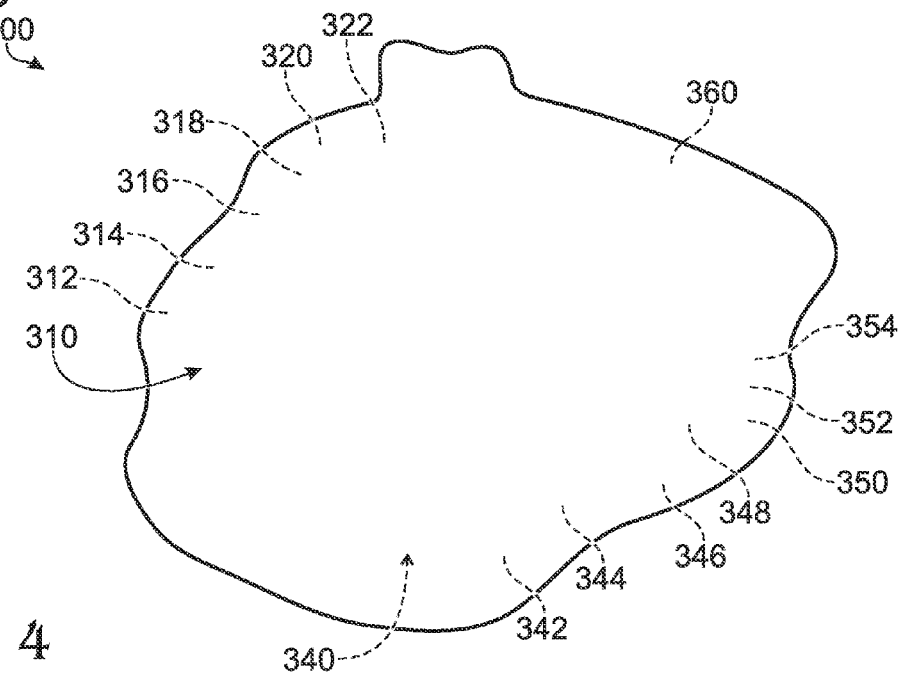
FIG. 1 is a schematic representation of illustrative, non-exclusive examples of a first bioremediation formulation that may be utilized with the systems and methods according to the present disclosure.

The systems, compositions, and methods disclosed herein include a first bioremediation formulation that includes an ion exchange resin and a second bioremediation formulation that is configured or adapted to provide at least a portion of the oxidants and nutrients that are utilized by a microbial population to support anaerobic respiration. The bioremediation formulations and systems and methods that include the bioremediation formulations are illustrated in the included Figures. Unless indicated otherwise, elements shown in dashed lines, or indicated with dashed lead lines, are considered to be optional features, structures, and/or steps. Elements shown in solid lines, or indicated with solid lead lines, are typically included in the systems, compositions, and methods disclosed herein; however, elements shown in dashed lines and/or those shown in solid lines may be omitted from a particular embodiment without departing from the scope of the present disclosure. In addition, the individual features, structures, and/or steps disclosed herein may be organized in any suitable fashion without departing from the scope of the present disclosure.

The systems, compositions, and methods disclosed herein promote the anaerobic oxidative bioremediation of a contaminant that is contained within a contaminated region by stimulating the normal life function of a microbial population that is associated with, present within, and/or naturally occurring within the contaminated region. The stimulating includes supplying at least a portion of the oxidants and nutrients that are used by the microbial population as part of its natural respiratory process. The disclosed systems, compositions, and methods encourage the consumption of the contaminant as a carbon and/or energy source, which also may be referred to herein as a food source, for the microbial population, thereby decreasing the concentration of the contaminant within the contaminated region.

The bioremediation formulations disclosed herein may include both active and inactive components. As used herein, active components may refer to components of the bioremediation formulations that are actively utilized during microbial respiration and/or components of the bioremediation formulations that actively participate in the delivery of the bioremediation formulations to the microorganisms, contaminant, treatment zone, and/or contaminated region.

In contrast, inactive components may refer to components of the bioremediation formulations that are not actively utilized during microbial respiration and/or components of the bioremediation formulations that do not actively participate in the delivery of the bioremediation formulations to the microorganisms, contaminant, treatment zone, and/or contaminated region.

The amount, proportion, or percentage of a particular component of the bioremediation formulations may be expressed as a weight percentage (wt %) of that component. It is within the scope of the present disclosure that when the bioremediation formulations include inactive components, the weight percentage may refer to a weight percentage of the active components contained within the bioremediation formulations and may not include the weight of the inactive components contained therein. Furthermore, when the bioremediation formulations form a liquid solution, an illustrative, non-exclusive example of which is an aqueous solution, it is within the scope of the present disclosure that the weight percentage may refer to the weight percentage of the solute contained within the liquid solution and/or a weight percentage of the dry components that are contained within the liquid solution.

As used herein, the terms microbe and microorganism may be used interchangeably and may refer to any suitable microscopic life form that may be present within the treatment zone and/or the contaminated region and may be adapted to consume, degrade, or otherwise decompose contaminants contained therein. Illustrative, non-exclusive examples of microorganisms according to the present disclosure include any suitable bacteria, such as *pseudomonas* species, *bacillus* species, and/or *E. coli* species, fungi, denitrifier, sulfate reducer, anaerobic species, facultative anaerobic species, and/or facultative aerobic species. Illustrative, non-exclusive examples of contaminants according to the present disclosure include hydrocarbons, petroleum hydrocarbons, metals, partially halogenated solvents, partially halogenated organics, benzene, ethyl benzene, toluene, xylene, gasoline, diesel, oil, and/or vinyl chloride.

As discussed in more detail herein, the disclosed systems, compositions, and methods may include multiple oxidants that include multiple oxidant mobilities within the treatment zone, as well as multiple oxidant energy states. This variation in oxidant mobility and oxidant energy state may provide for stimulation and/or growth of a wide variety of microorganisms over both long and short time frames and covering both long and short length scales within the treatment zone, providing a more effective overall bioremediation treatment. As an illustrative, non-exclusive example, the systems, compositions, and methods disclosed herein may stimulate the simultaneous growth of a plurality of microorganisms, including denitrifying, iron-related, and/or sulfate reducing bacteria to simultaneously consume a plurality of contaminants, including metals, benzene, ethyl benzene, toluene, and/or xylene.

As used herein, anaerobic respiration refers to respiratory processes that occur without the consumption, or without substantial consumption, of molecular oxygen. Instead, these anaerobic respiratory processes include the use of another suitable electron acceptor, or oxidant, to accept the electrons that are removed from the food source during the respiratory process. Illustrative, non-exclusive examples of suitable oxidants according to the present disclosure include nitrate ions, ionized metals, such as manganese (IV) and/or iron (III), sulfate ions, and/or carbon dioxide.

In general, anaerobic respiratory processes are less efficient, or slower, than aerobic respiratory processes, which utilize molecular oxygen as an electron acceptor, since a greater amount of energy is available to the microbial population when oxygen is utilized as an electron acceptor. However, certain microbes may only be capable of performing anaerobic respiratory processes. Also, certain treatment zones may contain little or no naturally occurring molecular oxygen and supplying molecular oxygen to the treatment zone may not be practical. In addition, and when the treatment zone includes an aqueous environment, a solubility of molecular oxygen within the aqueous environment may be orders of magnitude less than a solubility of another suitable oxidant, such as a salt, within the aqueous environment. Under these conditions, anaerobic respiratory processes may proceed more rapidly than aerobic respiratory processes due to the greater availability of reactants for the anaerobic respiratory processes within the aqueous environment and may therefore provide a more efficient overall bioremediation process.

Additionally or alternatively, and although anaerobic respiratory processes may be less efficient, or slower, that aerobic respiratory processes, the systems, compositions, and methods disclosed herein may provide for a rapid increase in a biomass of microbes within the treatment zone to a level that is significantly higher than a biomass that may be sustainable and/or supported by aerobic respiratory processes. This increase in microbe biomass may promote metabolism of contaminants that are contained within the treatment zone at a rate that is greater than a rate that may be attained using aerobic respiratory processes.

As used herein, the phrase "anaerobic oxidative bioremediation" refers to a bioremediation process that encourages anaerobic microbial respiration as a mechanism to promote the oxidation of, or removal of electrons from, the contaminant. As an illustrative, non-exclusive example, this may be accomplished by providing an abundance, or excess, of oxidants for the microbes to utilize during their respiratory processes.

FIG. 1 is a schematic representation of illustrative, non-exclusive examples of a first bioremediation formulation 300 that may be utilized with the systems and methods according to the present disclosure. First bioremediation formulation 300 includes an ion exchange resin 310. As illustrated in FIG. 1, first bioremediation formulation 300 also may include one or more additional components 340, illustrative, non-exclusive examples of which are discussed in more detail herein. Additional illustrative, non-exclusive examples of first bioremediation formulations 300 that may be utilized with the systems and methods according to the present disclosure are disclosed in U.S. Pat. No. 5,059,252, the complete disclosure of which is hereby incorporated by reference.

Ion exchange resin 310 may include any suitable material and/or composition that is adapted, configured, and/or synthesized to exchange one or more ions with its surroundings when placed in and/or part of an aqueous environment. As an illustrative, non-exclusive example, ion exchange resin 310 may include and/or be a cationic ion exchange resin 312.

As another illustrative, non-exclusive example, ion exchange resin 310 may include, be, and/or be formed from any suitable water-soluble ion exchange resin, water-soluble polymeric material, polymeric material, cross-linked polymeric material, and/or ion exchange polymeric material. This may include any suitable naturally occurring and/or synthetic polymeric material. Illustrative, non-exclusive examples of naturally occurring polymeric materials include cellulose and/or hemicellulose. Illustrative, non-exclusive examples of synthetic polymeric materials include synthetic polymeric materials that are synthesized from a styrene monomer, an acrylonitrile monomer, an acrylate ester monomer, and/or a methacrylate ester monomer. It is within the scope of the present disclosure that, when first bioremediation formulation 300 and/or ion exchange resin 310 thereof includes a polymeric material, the polymeric material may include and/or be functionalized with one or more electron-withdrawing groups, acid groups, and/or sulfonic acid groups.

It is within the scope of the present disclosure that ion exchange resin 310 may comprise any suitable portion of first bioremediation formulation 300. As an illustrative, non-exclusive example, the ion exchange resin may comprise at least 1 wt %, at least 2 wt %, at least 3 wt %, at least 4 wt %, at least 5 wt %, at least 6 wt %, at least 7 wt %, at least 8 wt %, at least 9 wt %, or at least 10 wt % of the first bioremediation formulation. Additionally or alternatively, the ion exchange resin may comprise less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, or less than 5 wt % of the first bioremediation formulation.

Ion exchange resin 310 may include any suitable structure. As illustrative, non-exclusive examples, the ion exchange resin may include and/or be a gel 314 and/or a macroreticular structure 316. As another illustrative, non-exclusive example, the ion exchange resin may be, be formed into, and/or be utilized as a bead 318, a sheet 320, and/or a powder 322.

Optional additional components 340 of first bioremediation formulations 300 may include any suitable compositions that may function as an active component of first bioremediation formulation 300. As an illustrative, non-exclusive example, additional components 340 may include and/or be a functionalized cyclic ring hydrocarbon 342, such as naphthalene that is functionalized with a cationic functional group, such as a mineral acid and/or sulfonic acid.

Additional components 340 also may include and/or be an acidulating agent 344, such as a mineral acid, sulfuric acid, buffered sulfuric acid, and/or hydrochloric acid. When first bioremediation formulation 300 includes an acidulating agent 344, the acidulating agent may comprise any suitable portion of the first bioremediation formulation. As an illustrative, non-exclusive example, the acidulating agent may comprise at least 60 wt %, at least 65 wt %, at least 70 wt %, at least 75 wt %, at least 80 wt %, or at least 85 wt % of the first bioremediation formulation. Additionally or alternatively, the acidulating agent may comprise less than 90 wt %, less than 85 wt %, less than 80 wt %, less than 75 wt %, less than 70 wt %, or less than 65 wt % of the first bioremediation formulation.

Additional components 340 further may include and/or be a surfactant 346, such as a sulfonated surfactant. When first bioremediation formulation 300 includes a surfactant 346, the surfactant may comprise any suitable portion of the first bioremediation formulation. As an illustrative, non-exclusive example, the surfactant may comprise at least 1 wt %, at least 2 wt %, at least 3 wt %, at least 4 wt %, at least 5 wt %, at least 6 wt %, at least 7 wt %, at least 8 wt %, at least 9 wt %, or at least 10 wt % of the first bioremediation formulation. Additionally or alternatively, the surfactant may comprise less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, or less than 5 wt % of the first bioremediation formulation.

Additional components 340 also may include and/or be an enzyme 348. When first bioremediation formulation 300 includes an enzyme 348, the enzyme may comprise any suitable portion of the first bioremediation formulation. As an illustrative, non-exclusive example, the enzyme may comprise at least 1 wt %, at least 2 wt %, at least 4 wt %, at least 6 wt %, at least 8 wt %, at least 10 wt %, at least 12 wt %, at least 14 wt %, at least 16 wt %, at least 18 wt % or at least 20 wt % of the first bioremediation formulation. Additionally or alternatively, the enzyme may comprise less than 30 wt %, less than 28 wt %, less than 26 wt %, less than 24 wt %, less than 22 wt %, less than 20 wt %, less than 18 wt %, less than 16 wt %, less than 14 wt %, less than 12 wt %, or less than 10 wt % of the first bioremediation formulation.

Additional components 340 further may include and/or be a ligno sulfate 350. When first bioremediation formulation 300 includes a ligno sulfate 350, the ligno sulfate may comprise any suitable portion of the first bioremediation formulation. As an illustrative, non-exclusive example, the ligno sulfate may comprise at least 1 wt %, at least 2 wt %, at least 4 wt %, at least 6 wt %, at least 8 wt %, at least 10 wt %, at least 12 wt %, at least 14 wt %, at least 16 wt %, at least 18 wt % or at least 20 wt % of the first bioremediation formulation. Additionally or alternatively, the ligno sulfate may comprise less than 30 wt %, less than 28 wt %, less than 26 wt %, less than 24 wt %, less than 22 wt %, less than 20 wt %, less than 18 wt %, less than 16 wt %, less than 14 wt %, less than 12 wt %, or less than 10 wt % of the first bioremediation formulation.

Additional components 340 also may include and/or be a binding agent 352. When first bioremediation formulation 300 includes a binding agent 352, the binding agent may comprise any suitable portion of the first bioremediation formulation. As an illustrative, non-exclusive example, the binding agent may comprise at least 1 wt %, at least 2 wt %, at least 4 wt %, at least 6 wt %, at least 8 wt %, at least 10 wt %, at least 12 wt %, at least 14 wt %, at least 16 wt %, at least 18 wt % or at least 20 wt % of the first bioremediation formulation. Additionally or alternatively, the binding agent may comprise less than 30 wt %, less than 28 wt %, less than 26 wt %, less than 24 wt %, less than 22 wt %, less than 20 wt %, less than 18 wt %, less than 16 wt %, less than 14 wt %, less than 12 wt %, or less than 10 wt % of the first bioremediation formulation.

Additional components 340 further may include and/or be a colloidal dispersant 354. When first bioremediation formulation 300 includes a colloidal dispersant 354, the colloidal dispersant may comprise any suitable portion of the first bioremediation formulation. As an illustrative, non-exclusive example, the colloidal dispersant may comprise at least 1 wt %, at least 2 wt %, at least 3 wt %, at least 4 wt %, at least 5 wt %, at least 6 wt %, at least 7 wt %, at least 8 wt %, at least 9 wt %, or at least 10 wt % of the first bioremediation formulation. Additionally or alternatively, the colloidal dispersant may comprise less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, or less than 5 wt % of the first bioremediation formulation.

It is within the scope of the present disclosure that first bioremediation formulation 300 may be formed, synthesized, present, and/or utilized in any suitable physical form. As an illustrative, non-exclusive example, the first bioremediation formulation may include and/or be a solid, such as beads 318, sheets 320, and/or powder 322. As another illustrative, non-exclusive example, the first bioremediation formulation may comprise, include, be present in, and/or form an aqueous first bioremediation solution that includes water 360 and the first bioremediation formulation.

When the first bioremediation formulation comprises the aqueous first bioremediation solution, the first bioremediation formulation may comprise any suitable proportion of the aqueous first bioremediation solution. As illustrative, non-exclusive examples, the first bioremediation formulation may comprise at least 0.01 wt %, at least 0.02 wt %, at least 0.04 wt %, at least 0.05 wt %, at least 0.06 wt %, at least 0.08 wt %, at least 0.1 wt %, at least 0.2 wt %, at least 0.3 wt %, at least 0.4 wt %, at least 0.6 wt %, at least 0.8 wt %, at least 1 wt %, at least 2 wt %, at least 4 wt %, at least 6 wt %, at least 8 wt %, at least 9 wt %, at least 10 wt %, at least 20 wt %, at least 30 wt %, at least 40 wt %, or at least 50 wt % of the aqueous first bioremediation solution. Additionally or alternatively, the first bioremediation formulation may comprise less than 60 wt %, less than 50 wt %, less than 40 wt %, less than 30 wt %, less than 20 wt %, less than 10 wt %, less than 9 wt %, less than 8 wt %, less than 6 wt %, less than 4 wt %, less than 2 wt %, less than 1 wt %, less than 0.8 wt %, less than 0.6 wt %, less than 0.4 wt %, less than 0.3 wt %, less than 0.2 wt %, or less than 0.1 wt % of the aqueous first bioremediation solution.

Figure 2:
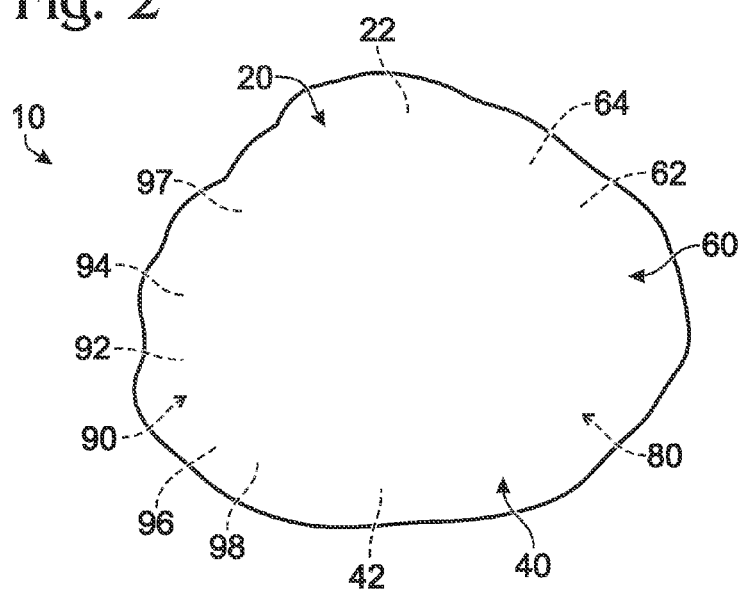
FIG. 2 is a schematic representation of illustrative, non-exclusive examples of a second bioremediation formulation according to the present disclosure.

FIG. 2 is a schematic representation of illustrative, non-exclusive examples of a second bioremediation formulation 10 according to the present disclosure. Second bioremediation formulation 10 includes at least a high-mobility oxidant 20, a low-mobility oxidant 40, and a nutrient material 60. In addition, and as shown in dashed lines in FIG. 2, the second bioremediation formulation optionally may include a mid-mobility oxidant 80 and/or at least a first additional component 90. As discussed in more detail herein, each of the individual components included within second bioremediation formulation 10 may be present in any suitable amount, proportion, or percentage, including the illustrative, non-exclusive examples presented herein.

As used herein, high-mobility oxidant 20 is a relative term that refers to an oxidant that has a higher mobility, or diffusion constant, within the treatment zone when compared to mid-mobility oxidant 80 or low-mobility oxidant 40. Similarly, mid-mobility oxidant 80 is a relative term that refers to an oxidant that has a higher mobility, or diffusion constant, within the treatment zone when compared to low-mobility oxidant 40 but a lower mobility, or diffusion constant, within the treatment zone when compared to high-mobility oxidant 20. The differences in oxidant mobilities may be caused by a variety of factors, including oxidant molecule diffusion constants, oxidant solubility, and/or oxidant affinity for one or more materials present within the treatment zone.

As an illustrative, non-exclusive example, high-mobility oxidants, such as nitrate salts, may be more soluble in water that may be present within the treatment zone when compared to mid- or low-mobility oxidants, such as sulfate salts. As another illustrative, non-exclusive example, and when the treatment zone includes soil, stone, and/or other geological structures, high-mobility oxidants may have a lower affinity for and/or attraction to the geological structures when compared to low-mobility oxidants. As yet another illustrative, non-exclusive example, mid and low-mobility oxidants, such as sulfate salts, may form low-solubility complexes with chemical species that are already present within the treatment zone, while high-mobility oxidants, such as nitrate salts, may be less likely to form the low-solubility complexes.

As discussed in more detail herein, the systems, compositions, and methods disclosed herein may include a mixture of oxidants that may include a range of oxidant mobilities within the treatment zone. This may include low-mobility oxidants, which may remain in, or substantially in, the portion of the treatment zone to which they are applied, as well as mid- and/or high-mobility oxidants, which may diffuse more rapidly throughout the treatment zone. The use of a mixture of oxidants that include a range of oxidant mobilities may provide localized, concentrated, and/or short timeframe bioremediation within an application site as well as a more dispersed bioremediation over longer distances and/or times.

High-mobility oxidants 20 may include any suitable composition, other than molecular oxygen, that is adapted to function as an oxidant, or electron acceptor, during the anaerobic microbial respiration process and that is highly mobile within the treatment zone when compared to low- and/or mid-mobility oxidants. The high-mobility oxidant may comprise any suitable proportion of second bioremediation formulation 10, illustrative, non-exclusive examples of which include high-mobility oxidants that comprise 0-50 wt % of the second bioremediation formulation, optionally comprising 0-40 wt %, 1-50 wt %, 1-45 wt %, 1-40 wt %, 10-40 wt %, 10-30 wt %, 5-10 wt %, 5-15 wt %, 5-20 wt %, 10-20 wt %, or 20-30 wt % of the second bioremediation formulation.

Illustrative, non-exclusive examples of high-mobility oxidants according to the present disclosure include nitrate salts 22. Illustrative, non-exclusive examples of nitrate salts 22 according to the present disclosure include potassium nitrate, sodium nitrate, magnesium nitrate, cobalt nitrate, calcium nitrate, ammonium nitrate, ammonium phosphate nitrate, ammonia-ammonium nitrate, calcium ammonium nitrate, urea-ammonium nitrate, zinc nitrate, iron nitrate, manganese nitrate, cupric nitrate, and nitrate of soda potash.

These and other nitrate salts may be present within second bioremediation formulation 10 individually or in combination. Thus, it is within the scope of the present disclosure that second bioremediation formulations 10 disclosed herein, including the high-mobility oxidants included within the second bioremediation formulations, may include a blend of nitrate salts. When present as a combination, or blend, of nitrate salts, each of the individual nitrate salts present within the second bioremediation formulation may comprise any suitable proportion of the second bioremediation formulation, including the illustrative, non-exclusive examples of high-mobility oxidant weight percentages listed above.

As an illustrative, non-exclusive example, second bioremediation formulations 10 according to the present disclosure may include potassium nitrate, magnesium nitrate, and sodium nitrate and/or calcium nitrate. Magnesium ions exert minimal osmotic pressure on cell walls because they readily adhere to the soil matrix and/or are readily incorporated into biomass. In addition, magnesium ions may combine with sulfides present within the contaminated region, precipitating them from solution and decreasing unpleasant odors within any water contained therein. Potassium ions exert an osmotic pressure on cell walls that is opposite that of sodium and, when available to microbes, may increase tolerance to high concentrations of volatile fatty acids, thus improving microbe survival. In addition, sodium and/or calcium ions, when available to microbes, may improve the tolerance of the microbes to exposure to ammonia, which may be present in the second bioremediation formulation and provided to the treatment zone.

Thus, the use of a blend of nitrate salts may improve water quality and/or decrease a potential for microbe growth inhibition and/or microbe mortality due to: (1) high sodium levels that may be present if sodium nitrate were used as the sole nitrate source, (2) high volatile fatty acid concentrations within the contaminated region, and/or (3) the inclusion of ammonia as a nitrogen source within the second bioremediation formulation. This may provide for the use of higher overall second bioremediation formulation concentrations within the treatment zone and increase a rate of contaminant consumption within the treatment zone. These second bioremediation formulation concentrations, which are discussed in more detail herein, may be one or more orders of magnitude higher than the concentrations that would be permissible without utilizing a blend of nitrate salts and/or if the nitrate species disclosed herein were supplied as a nutrient for an aerobic bioremediation process as opposed to being supplied as an oxidant for anaerobic oxidative bioremediation.

Mid-mobility oxidants 80 include any suitable composition, other than molecular oxygen, that is adapted to function as an oxidant, or electron acceptor, during the anaerobic microbial respiration process and that is less mobile within the treatment zone when compared to high-mobility oxidants but more mobile within the treatment zone when compared to low-mobility oxidants. Similarly, low-mobility oxidants 40 include any suitable composition, other than molecular oxygen, that is adapted to function as an oxidant, or electron acceptor, during the anaerobic microbial respiration process, and that is less mobile within the treatment zone when compared to mid- and/or high-mobility oxidants. The mid- and/or low-mobility oxidants may comprise any suitable proportion of second bioremediation formulation 10, illustrative, non-exclusive examples of which include mid- and/or low-mobility oxidants that comprise 0-70 wt % of the second bioremediation formulation, optionally including 0-30 wt %, 0-40 wt %, 1-70 wt %, 1-65 wt %, 1-60 wt %, 1-40 wt %, 1-30 wt %, 10-60 wt %, 20-60 wt %, 10-30 wt %, 5-10 wt %, 5-15 wt %, 10-20 wt %, 20-30 wt %, 20-40 wt %, or 25-35 wt % of the second bioremediation formulation.

Illustrative, non-exclusive examples of mid-mobility oxidants 80 and/or low-mobility oxidants 40 according to the present disclosure include sulfate salts 42. Illustrative, non-exclusive examples of sulfate salts according to the present disclosure include calcium sulfate, magnesium sulfate, ammonium sulfate, zinc sulfate, iron sulfate, manganese sulfate, cupric sulfate, ammonium phosphate sulfate, ammonium sulfate, potassium sulfate, sulfate of potash magnesia, potassium thiosulfate, potassium zinc sulfate, magnesium bisulfate, cobalt sulfate, and cobaltous potassium sulfate. These and other sulfate salts may be present within second bioremediation formulation 10 individually or in combination. When present as a combination of sulfate salts, each of the individual salts present within the second bioremediation formulation may comprise any suitable proportion of the second bioremediation formulation, including the illustrative, non-exclusive examples of mid- and low-mobility oxidant weight percentages listed above.

In addition to providing second bioremediation formulations that may include a mixture of oxidants including a range of oxidant mobilities within the treatment zone, the systems, compositions, and methods disclosed herein also may include the use of a mixture of oxidants that may provide a range of oxidant energy states. As used herein the oxidant energy state refers to the amount of energy that is available to a microorganism when utilizing the oxidant as part of its respiratory processes. In general, oxidants with higher relative energy states will be preferentially utilized by microorganisms more quickly than oxidants with lower relative energy states due to the additional energy that is available to the microorganism when the higher energy state oxidant is consumed.

Aerobic respiration, which utilizes molecular oxygen as the oxidant, provides the largest amount of energy to microbes. However, and as discussed in more detail herein, aerobic respiration may not always be feasible and/or may not provide the greatest overall bioremediation rates due to the limited availability of molecular oxygen under certain circumstances. As discussed in more detail herein, anaerobic respiration utilizes a chemical species other than molecular oxygen as the electron acceptor, or oxidant, in the respiratory process. In general, nitrate species provide more energy than metals, such as manganese (IV) or iron (III), which provide more energy than sulfate species, which provide more energy than carbon monoxide. Thus, when the second bioremediation formulations 10 disclosed herein include both nitrate and sulfate salts, the nitrate salts may be consumed by the microorganisms more quickly than the sulfate salts.

As discussed in more detail herein, the use of ionic salts as an oxidant to support anaerobic microbial respiration may provide for supplying oxidants to the treatment zone at a concentration that is many orders of magnitude higher that what may be achievable when molecular oxygen is utilized as an oxidant to support aerobic microbial respiration. As an illustrative, non-exclusive example, and when the treatment zone includes water, the solubility of molecular oxygen in the water is approximately 0.0076 grams/liter (g/L) at 20° C. In contrast, the solubility of ionic salts in water may be much higher. As an illustrative, non-exclusive example, the solubility of sodium nitrate in water is approximately 876 g/L at 20° C., over five orders of magnitude higher. Other nitrate and/or sulfate salts may have solubilities of 5,000 g/L or more at 20° C. This higher oxidant solubility may provide a greater oxidant availability to the microbes present within the treatment zone, may decrease the potential for oxidant depletion within the treatment zone, and/or may provide for a decrease in the size of equipment that is utilized in the bioremediation process by decreasing a volume of material that may be moved, pumped, and/or otherwise handled as part of the bioremediation process.

In addition, and while it may be possible to supply molecular oxygen to a treatment zone through the direct delivery of oxygen and/or air to the treatment zone and/or through the injection of oxygen-releasing compounds into the treatment zone, this molecular oxygen may be consumed quickly due to its high energy state, may not remain in the treatment zone due to solubility limitations, and/or may be produced within the treatment zone at a rate that is dependent on local temperatures and pressures, as opposed to microorganism demand (as may be the case for oxygen-releasing compounds). In contrast, the oxidants disclosed herein, which take the form of ionic salts, may exist at high concentrations within the treatment zone and may persist within the treatment zone until they are consumed by microorganisms to support their respiratory processes. Thus, the systems, compositions, and methods disclosed herein may provide a more targeted and efficient oxidant delivery mechanism when compared to delivery of molecular oxygen to the treatment zone. In addition, the slower consumption of the ionic salts may decrease the potential for damage to the microbial population due to high oxidant concentrations, increasing a threshold oxidant concentration within the treatment zone above which the oxidant may damage, or inhibit the growth of, the microbial population.

In contrast with oxidants, which are utilized to accept electrons during microbial respiration, nutrient material 60 may provide a portion of the energy, or food, utilized to support microbial respiration. In general, second bioremediation formulations may be designed and supplied to the treatment zone in a way that encourages, or promotes, consumption of the contaminant as a food, or energy, source for the microorganisms present therein. However, the contaminant may not include a source of nutrients that will support a target, or desired, rate and/or extent of microbe growth and/or biomass formation. Thus, it is within the scope of the present disclosure that second bioremediation formulations 10 disclosed herein may include or contain any suitable additional nutrient 60 that may supplement or otherwise augment microbial respiration.

It is within the scope of the present disclosure that nutrients 60 may be selected to accomplish any suitable purpose. As an illustrative, non-exclusive example, the nutrients may be selected to increase a rate of contaminant consumption within the treatment zone. As another illustrative, non-exclusive example, the nutrients may be selected to increase a rate and/or extent of microbial biomass formation within the treatment zone. As yet another illustrative, non-exclusive example, the nutrients may be selected to encourage a certain respiratory process over another respiratory process. Illustrative, non-exclusive examples of respiratory processes according to the present disclosure include respiratory processes that form biomass and respiratory processes that produce energy for the microorganisms. As yet another illustrative, non-exclusive example, nutrients 60 may be selected to supplement, or augment, the naturally occurring nutrients that are already present within a subsurface region that includes the contaminants. Nutrients 60 may include macronutrients, which may be utilized in large quantities by the microorganisms, as well as micronutrients, which may be utilized in relatively smaller quantities by the microorganisms. As yet another illustrative, non-exclusive example, nutrients 60 may be selected to function as a growth substrate for the microorganisms.

Illustrative, non-exclusive examples of macronutrients according to the present disclosure include nitrogen, ammonium, phosphorous, phosphate, pyrophosphate, and/or potassium. Illustrative, non-exclusive examples of micronutrients according to the present disclosure include iron, magnesium, zinc, copper, manganese, selenium, and/or B-vitamins. These nutrients may be provided from chemically and/or biologically derived sources to provide the nitrogen, phosphorus, potassium, and/or micronutrients needed to support microbial respiration at the desired, or target, growth rates. In addition to these individual nutrients, second bioremediation formulations 10 according to the present disclosure may include materials that may provide a plurality of nutrients to the microorganisms. Illustrative, non-exclusive examples of materials that may provide a plurality of nutrients to the microorganisms include brewer's yeast 62 and/or complex sugars 64.

Brewer's yeast 62 may be present within a second bioremediation formulation 10 in any suitable amount, proportion, or percentage, and may provide micronutrients and/or macronutrients to the microorganisms. Brewer's yeast is a type of fungus that may be used in the manufacture of bread and/or beer and/or may be obtained as a byproduct of a brewing process. As an illustrative, non-exclusive example, brewer's yeast may include yeast from the genus *Saccharomyces*, such as the yeast *Saccharomyces cerevisiae*.

Brewer's yeast is available in both active and inactive forms. In its active form, brewer's yeast may ferment carbohydrates when it comes into contact with them, forming carbon dioxide. In contrast with other yeast products, such as yeast extract, brewer's yeast includes an intact cell wall. This intact cell wall may increase the stability of the nutrients supplied by the brewer's yeast within the treatment zone, may serve as a complex sugar source for the microbes, and/or may provide for a longer residence time within the treatment zone and/or a more targeted delivery of nutrients to the microorganisms present therein. However, it is also within the scope of the present disclosure that other yeast products, including yeast extract, may be utilized with the systems, compositions, and methods disclosed herein.

Brewer's yeast, another suitable yeast product, such as yeast extract, or combinations thereof may be included within second bioremediation formulation 10 in any suitable amount or proportion. As an illustrative, non-exclusive example, brewer's yeast may comprise 1-20 wt % of a second bioremediation formulation, optionally comprising 2-18 wt %, 3-17 wt %, 5-15 wt %, 7-12 wt %, 5-10 wt %, or 10-15 wt % of the second bioremediation formulation.

One or more complex sugars 64 also may be present in second bioremediation formulations 10 according to the present disclosure in any suitable amount, proportion, or percentage. These complex sugars may improve the growth and/or maintenance of the microorganisms present within the treatment zone by acting as a microbial nutrient and/or growth substrate. Complex sugars may include various degrees of molecular branching and/or substitution and may provide a slow-release sugar source within the treatment zone. Illustrative, non-exclusive examples of complex sugars according to the present disclosure include polysaccharides, ribose, sugar-protein complexes, glycoproteins, α-bonded polysaccharides, starches, amylopectin, β-bonded polysaccharides, cellulose, carboxymethylcellulose, modified β-bonded polysaccharides, and chitin.

A specific complex sugar 64 or a plurality of complex sugars 64 may be utilized within second bioremediation formulations 10 to tailor the bioavailability of the complex sugar, or sugars, and thus the rate at which the complex sugars may be consumed by microorganisms. As an illustrative, non-exclusive example, α-bonded polysaccharide molecules, such as starches, typically include some degree of branching and are readily digestible by many microorganisms. However, the digestion rate may be slowed through the use of cross-linked, α-bonded polysaccharide molecules such as pectin or amylopectin. In contrast, β-bonded polysaccharides, such as cellulose, must undergo spontaneous hydrolysis or be digested by specialized enzymes to release individual glucose molecules. This may slow the rate at which they may be consumed by the microorganisms present within the treatment zone and/or may extend their longevity within the treatment zone. Modified β-bonded polysaccharides such as chitin and carboxymethylcellulose may be consumed by microorganisms even more slowly.

Complex sugar 64 may be present within second bioremediation formulations 10 in any suitable amount or proportion. As an illustrative, non-exclusive example, the complex sugar may comprise 1-20 wt % of a second bioremediation formulation, optionally comprising 1-2 wt %, 1-3 wt %, 3-5 wt %, 3-7 wt %, 2-18 wt %, 3-17 wt %, 5-15 wt %, 7-12 wt %, 5-10 wt %, or 10-15 wt % of the second bioremediation formulation. One or more complex sugars may be present within second bioremediation formulations 10 individually or in combination. When present in combination, each of the individual complex sugars present within a second bioremediation formulation may comprise any suitable proportion of the second bioremediation formulation, including any of the illustrative, non-exclusive examples of complex sugar proportions listed above.

As discussed, second bioremediation formulations 10 also may optionally include additional components 90, illustrative, non-exclusive examples of which include one or more phosphate salts 92, one or more surfactants 94, one or more solvents 96, and/or one or more bio-augmentation species 98. The additional components may include components that may be consumed during microbial respiration, as well as components that may increase the availability of nutrients and/or contaminants to microorganisms present within the treatment zone, such as through solvation, dissolution, and the like.

Illustrative, non-exclusive examples of phosphate salts 92, which also may be referred to herein as phosphates 92, according to the present disclosure include diammonium phosphate, ammonium phosphate, and tetrapotassium phosphate. Phosphate salt 92 may provide a source of elemental phosphorous that may be utilized by the microorganisms during respiration and may be present within the second bioremediation formulation in any suitable proportion or amount. As an illustrative, non-exclusive example, the phosphate salt may comprise 1-40 wt % of the second bioremediation formulation, optionally comprising 5-35 wt %, 10-30 wt %, 10-20 wt %, 20-30 wt %, 15-25 wt %, or 18-22 wt % of the second bioremediation formulation. The phosphate salts may be present within a second bioremediation formulation individually or in combination. When present in combination, each of the individual phosphate salts present within a second bioremediation formulation may comprise any suitable proportion of the second bioremediation formulation, including any of the illustrative, non-exclusive examples of phosphate salt proportions listed above.

Second bioremediation formulations 10 according to the present disclosure also may include at least one surfactant 94, at least one solvent 96, at least one chemical oxidant 97, and/or at least one bio-augmentation species 98. Illustrative, non-exclusive examples of surfactants 94 according to the present disclosure include ionic surfactants and non-ionic surfactants. Surfactants, when present, may increase a water solubility of at least a portion of second bioremediation formulation 10 and/or at least a portion of the contaminant, which may increase a potential for contact among the microorganisms, the second bioremediation formulation, and/or the contaminant within the treatment zone and increase the rate of contaminant consumption. Solvents 96 may perform a similar function to that of surfactant 94. Illustrative, non-exclusive examples of solvents 96 according to the present disclosure include water, as well as suitable co-solvent mixtures.

Chemical oxidants 97 may directly oxidize contaminants present within the treatment zone without the need for and/or use of a microorganism as an intermediary. It is within the scope of the present disclosure that chemical oxidants 97, when present, may not be consumed by the microorganisms present within the treatment zone. However, it is also within the scope of the present disclosure that the chemical oxidants may chemically oxidize contaminants and also be consumed by the microorganisms present within the treatment zone as at least one of a nutrient and an oxidant.

As discussed in more detail herein, bio-augmentation species 98 may include microorganisms that are selected, created, and/or propagated based upon their enhanced ability to consume a particular, or target, contaminant that may be present within the treatment zone. Thus, the addition of bio-augmentation species 98 to the second bioremediation formulations disclosed herein may increase a rate of consumption of the target contaminant within the treatment zone.

Any suitable criteria may be utilized to select an appropriate, desired, and/or target amount or proportion for a given component and/or group of components within a second bioremediation formulation 10. This may include criteria that may be based upon site-specific conditions at the contaminated site, handling and/or storage constraints, estimated microbial nutrient demand, hydraulic characteristics of the contaminated site, geochemical characteristics of the contaminated site, geologic characteristics of the contaminated site, and/or the nature of the contaminants present within the contaminated site.

As an illustrative, non-exclusive example, a mass of the second bioremediation formulation provided to the treatment zone may be calculated based, at least in part, upon a mass of contaminant present within the treatment zone and/or the contaminated region. As another illustrative, non-exclusive example, the mass of the second bioremediation formulation provided to the treatment zone may be calculated based, at least in part, on a mass of contaminant that may be removed from the treatment zone to bring a concentration of contaminant within the treatment zone into compliance with regulatory requirements. This may include providing less second bioremediation formulation to the treatment zone than would be needed to consume all of the contaminants that may be contained therein.

As another illustrative, non-exclusive example, the mass of second bioremediation formulation provided to the treatment zone may be calculated based, at least in part, on a mass of competing electron donors that may be present within the treatment zone and/or the contaminated region. As yet another illustrative, non-exclusive example, the mass of second bioremediation formulation provided to the treatment zone may be calculated based, at least in part, on the mass of the contaminant and the mass of the competing electron donors that may be present within the treatment zone and/or the contaminated region.

Illustrative, non-exclusive examples of the mass of the second bioremediation formulation that may be provided to the treatment zone include masses of at least 0.2, at least 0.4, at least 0.5, at least 0.6, at least 0.7, at least 0.8, at least 1, at least 1.5, at least 2, at least 2.5, at least 3, at least 3.5, at least 4, at least 4.5, or at least 5 kilograms of the second bioremediation formulation for each kilogram of the contaminant. Additionally or alternatively, the mass of the second bioremediation formulation that may be provided to the treatment zone may include masses of less than 10, less than 9.5, less than 9, less than 8.5, less than 8, less than 7.5, less than 7, less than 6.5, less than 6, less than 5.5, less than 5, less than 4.5, less than 4, less than 3.5, less than 3, or less than 2.5 kilograms of the second bioremediation formulation for each kilogram of the contaminant. However, values outside these ranges are also within the scope of the present disclosure.

As used herein, the phrase "competing electron donors" may refer to materials other than the contaminant that may provide electrons to, and thus consume, the oxidants present within the second bioremediation formulation. Illustrative, non-exclusive examples of competing electron donors according to the present disclosure include manganese (III), iron (II), sulfide, methane, hydrogen, and/or volatile fatty acids.

The proportion of components contained within a second bioremediation formulation 10 may be selected to provide a desired, specific, and/or target nitrogen to phosphorous ratio within the second bioremediation formulation. This may include target nitrogen to phosphorous ratios of between 2:1 and 8:1, such as target nitrogen to phosphorous ratios between 3:1 and 6:1, as well as nitrogen to phosphorous ratios of approximately 3.5:1, 4:1, 4.5:1, 5:1, or 5.5:1. Other ratios, or proportions, are also within the scope of the present disclosure. Higher phosphorous concentrations may be utilized with the systems, compositions, and methods disclosed herein when compared to more traditional bioremediation formulations, which may include a nitrogen to phosphorous ratio of approximately 10:1, to encourage the formation of microorganism biomass within the treatment zone.

Second bioremediation formulations 10 disclosed herein may be created, stored, and/or supplied to the treatment zone in any suitable form. As an illustrative, non-exclusive example, the second bioremediation formulations may include dry bioremediation formulations. Illustrative, non-exclusive examples of dry bioremediation formulations include powdered, granular, and/or pellet forms. These dry bioremediation formulations may include substantially heterogeneous or substantially homogeneous mixtures. When a second bioremediation formulation 10 includes a dry bioremediation formulation, it is within the scope of the present disclosure that the dry bioremediation formulation may include a coating or other time-release structure adapted or configured to control a rate of delivery of the second bioremediation formulation to the treatment zone.

Second bioremediation formulations 10 disclosed herein also may include solutions of the second bioremediation formulations. An illustrative, non-exclusive example of a solution of a second bioremediation formulation according to the present disclosure includes an aqueous solution of the second bioremediation formulation. When the second bioremediation formulation is included in an aqueous solution, the aqueous solution may include any suitable amount or proportion of the second bioremediation formulation. As an illustrative, non-exclusive example, the aqueous solution may include 5-65 wt % of the second bioremediation formulation, including 5-50 wt %, 5-40 wt %, 5-30 wt %, 5-20 wt %, 5-15 wt %, 5-10 wt %, 10-25 wt %, 10-20 wt %, 10-15 wt %, approximately 11 wt %, approximately 12 wt %, approximately 13 wt %, approximately 14 wt %, or approximately 15 wt % of the second bioremediation formulation. Other weight percentages are also within the scope of the present disclosure.

Figure 3:
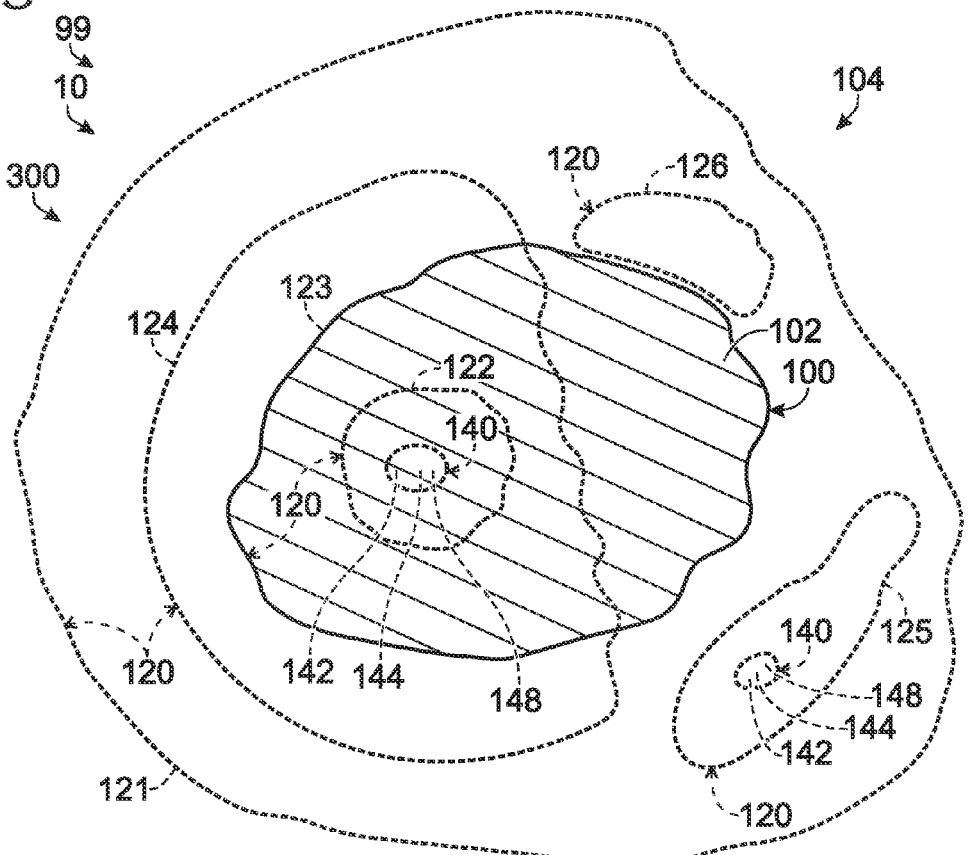
FIG. 3 is a schematic plan view representing illustrative, non-exclusive examples of a treatment zone associated with a contaminated region that may be utilized with the systems and methods according to the present disclosure.

FIG. 3 provides a plan view of an illustrative, non-exclusive example of a contaminated site 99 that includes a contaminated region 100 according to the present disclosure. Contaminated region 100 may include or contain a contaminant 102 and may be associated with one or more treatment zones 120. As used herein, the phrase "associated with" means that at least a portion of treatment zone 120 may be proximal to, in fluid communication with, in physical contact with, contained within, and/or contain at least a portion of contaminated region 100. The contaminated region also may include and/or contain one or more microorganisms 104 that may be adapted to consume contaminant 102 as part of their natural respiratory processes.

It is within the scope of the present disclosure that treatment zone 120 may be associated with contaminated region 100 in any suitable manner. As an illustrative, non-exclusive example, and with reference to FIG. 3, treatment zone 120 may include and/or contain all of contaminated region 100 as shown at 121. As another illustrative, non-exclusive example, treatment zone 120 may be completely included and/or contained within contaminated region 100 as shown at 122. As yet another illustrative, non-exclusive example, treatment zone 120 may be coextensive with contaminated region 100 as shown at 123. As yet another illustrative, non-exclusive example, treatment zone 120 may include and/or contain a portion of contaminated region 100 as shown at 124. As yet another illustrative, non-exclusive example, treatment zone 120 may be proximal to and/or form a barrier around at least a portion of contaminated region 100 as shown at 125. As yet another illustrative, non-exclusive example, treatment zone 120 may be adjacent to at least a portion of contaminated region 100 as shown at 126.

When the treatment zone is proximal to and/or forms a barrier around at least a portion of the contaminated region as shown at 125 and/or when the treatment zone is adjacent to the contaminated region as shown at 126, the treatment zone may be located to decrease a migration of contaminants away from contaminated region 100 and/or to increase treatment of contaminated region 100. As an illustrative, non-exclusive example, and when there is a flow of water, such as groundwater, through the contaminated region, treatment zone 120 may be located downstream of the contaminated region and may serve as a permeable reactive barrier to decrease the potential for contaminant migration away from the contaminated region. Additionally or alternatively, treatment zone 120 may be located upstream of the contaminated region, may mix with the flow of water, and may serve to provide a supply of bioremediation formulation(s) 10 and/or 300 to the contaminated region as bioremediation formulation(s) 10 and/or 300 are carried from the treatment zone to the contaminated region by the flow of water, expanding the size of the treatment zone.

It is within the scope of the present disclosure that bioremediation formulations 10 and/or 300 disclosed herein may be present within and/or applied to the treatment zone and/or the contaminated region in any suitable manner. As an illustrative, non-exclusive example, bioremediation formulations 10 and/or 300 may be uniformly, or substantially uniformly, distributed throughout the treatment zone. Bioremediation formulations 10 and/or 300 that are uniformly distributed throughout the treatment zone may be uniformly distributed at the time of introduction into the treatment zone, such as by being uniformly mixed into the treatment zone. Additionally or alternatively, bioremediation formulations 10 and/or 300 may be uniformly distributed over time by diffusion and/or fluid flows within the treatment zone.

Bioremediation formulations 10 and/or 300 also may exhibit a concentration gradient across the treatment zone. As an illustrative, non-exclusive example, and with continued reference to FIG. 3, a bioremediation formulation 10 and/or 300 may be initially applied to the treatment zone at one or more application sites 140, such as any suitable borehole 142, well 144, and/or infiltration gallery 148. Bioremediation formulations 10 and/or 300 may then diffuse, flow, or otherwise move from the initial application site with time. This movement may be based, at least in part, on the mobility of the individual components that comprise bioremediation formulation 10 and/or 300, as discussed in more detail herein.

As an illustrative, non-exclusive example, and when second bioremediation formulation 10 includes a high-mobility oxidant 20 and a low-mobility oxidant 40, the high-mobility oxidant may move away from the application site more quickly than the low-mobility oxidant, increasing the overall size of a treatment zone 120. Similarly, the low-mobility oxidant may diffuse more slowly than the high-mobility oxidant and/or may remain within, or substantially within, the application site. Thus, second bioremediation formulations 10 according to the present disclosure may provide directed, or controlled, oxidant availability over a variety of length scales, or distances, within the treatment zone.

Contaminated region 100 may include any suitable region or structure that may include or contain contaminant 102. Illustrative, non-exclusive examples of contaminated regions according to the present disclosure include aquifers, lakes, rivers, streams, soil samples, soil samples that have been removed from a contaminated site, fields, parking areas, industrial sites, commercial sites, waste disposal sites, and/or landfills. These contaminated regions include contaminant 102 and also may include liquids, such as water, as well as solids, such as biomass, soil, and/or rocks.

Bioremediation formulations 10 and/or 300 may be supplied to treatment zone 120 using any suitable method or mechanism. As an illustrative, non-exclusive example, and when contaminated region 100 includes an aquifer, lake, river, stream, and/or another site that includes water, bioremediation formulations 10 and/or 300 may be supplied to the treatment zone as an aqueous solution. This may include slug injecting aqueous solutions of the bioremediation formulations 10 and/or 300 using any suitable well 144, monitoring well, injection well, shallow well that includes a terminal depth that is above the saturated zone and/or within a vadose zone of the subsurface region, vapor extraction well, borehole 142, infiltration gallery 148, horizontal slotted pipe, direct push technology, lance injection technology, and/or push probe, which may form a portion of and/or be application site 140.

Additionally or alternatively, it is within the scope of the present disclosure that bioremediation formulations 10 and/or 300 may be supplied to the treatment zone as part of a groundwater recirculation treatment in which groundwater may be pumped from a suitable subsurface region, combined with bioremediation formulations 10 and/or 300, and returned to the treatment zone. It is also within the scope of the present disclosure that bioremediation formulations 10 and/or 300 disclosed herein may be utilized to provide oxidative treatment of the treatment zone during air sparging applications in which air, molecular oxygen, ozone, or other gaseous oxidants are injected directly into the treatment zone and/or the groundwater.

As another illustrative, non-exclusive example, and when contaminated region 100 includes a soil sample, field, parking area, industrial site, commercial site, waste disposal site, or other surface or near-surface region, bioremediation formulations 10 and/or 300 may be applied to the treatment zone as an aqueous solution and/or as a dry bioremediation formulation, including any of the dry bioremediation formulations disclosed herein. When bioremediation formulations 10 and/or 300 are applied to the treatment zone as an aqueous solution, they may be sprayed, injected, irrigated, flooded, and/or chemigated onto the treatment zone. When bioremediation formulations 10 and/or 300 are applied to the treatment zone as a dry bioremediation formulation, they may be spread onto, broadcast onto, and/or mixed into the treatment zone utilizing any suitable process.

Figure 4:
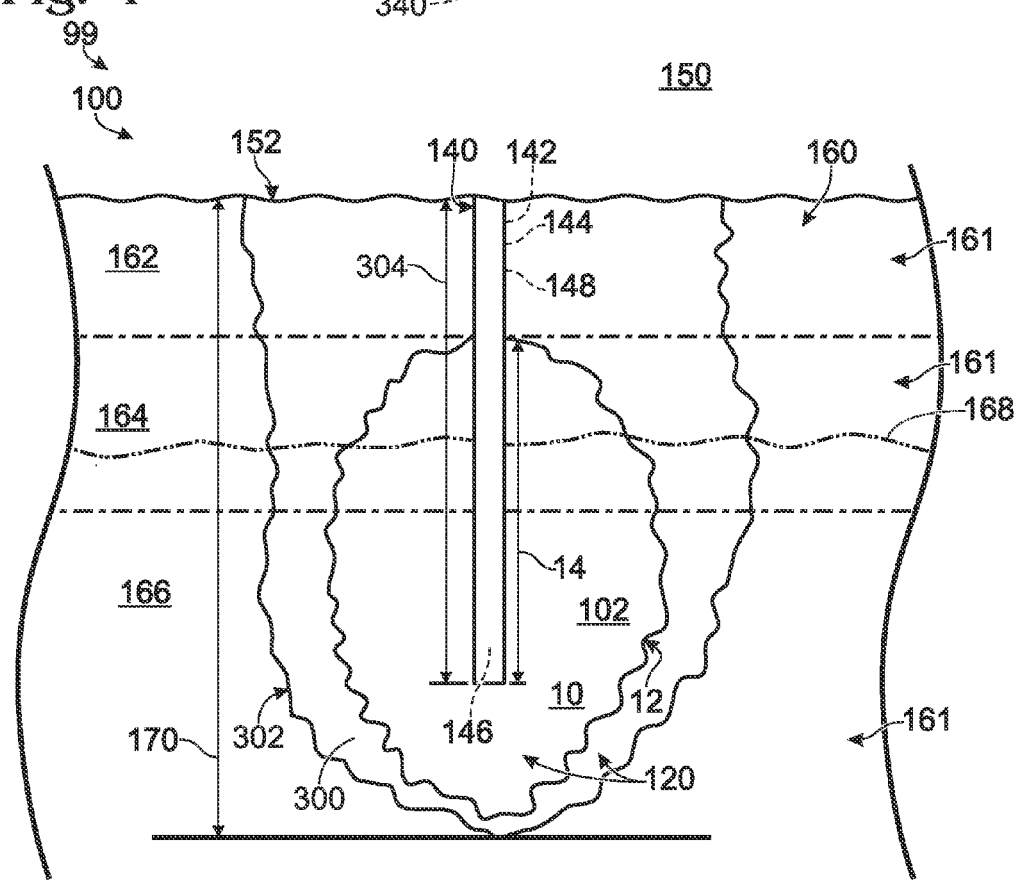
FIG. 4 is a schematic cross-sectional side view representing illustrative, non-exclusive examples of a treatment zone associated with a contaminated region that may be utilized with the systems and methods according to the present disclosure.

FIG. 4 provides a schematic cross-sectional side view of illustrative, non-exclusive examples of treatment zones 120 that are associated with a contaminated site 99 that includes a contaminated region 100. Contaminated region 100 includes a contaminant 102 therein. In FIG. 4, application site 140 may include borehole 142, well 144, and/or infiltration gallery 148 and extends between a surface region 150 and a subsurface region 160. Subsurface region 160 may include a plurality of zones 161, including a vadose zone 162, a smear zone 164, and a saturated zone 166 (which are separated by dash-dot lines in FIG. 4).

Vadose zone 162 is an aerated region above water table 168 and extends between surface region 150 and smear zone 164. Smear zone 164 is a transition region between vadose zone 162 and saturated zone 166 that is saturated with water during part of the year and aerated part of the year, depending upon the height of water table 168 (which is indicated by dash-dot-dot lines in FIG. 4) at a given time of year. Saturated zone 166 includes a region below smear zone 164 that is saturated (i.e., below water table 168) year-round.

As discussed in more detail herein, systems and methods according to the present disclosure may include injecting, providing, and/or otherwise supplying a bioremediation formulation, such as first bioremediation formulation 300 and/or second bioremediation formulation 10, to and/or within any suitable zone(s) 161 and/or to any suitable total treatment depth 170 within subsurface region 160.

As an illustrative, non-exclusive example, and as shown in FIG. 4, the systems and methods according to the present disclosure may include supplying first bioremediation formulation 300 to a first treatment zone 302 of subsurface region 160 that extends between ground surface 152 and total treatment depth 170. This may include supplying the first bioremediation formulation to and/or along a first length 304 of application site 140 and/or borehole 142, well 144, and/or infiltration gallery 148 thereof.

In addition and as also illustrated in FIG. 4, the systems and methods also may include supplying second bioremediation formulation 10 to a second treatment zone 12 of subsurface region 160 that extends between the top of smear zone 164 and total treatment depth 170. This may include supplying the second bioremediation formulation to and/or along a second length 14 of application site 140 and/or borehole 142, well 144, and/or infiltration gallery 148 thereof. Furthermore, and subsequent to supplying first bioremediation formulation 300 and second bioremediation formulation 10 to subsurface region 160, the systems and methods also may include backfilling application site 140 with a sealing material 146, such as bentonite and/or concrete.

Similar to the discussion that is contained herein with reference to FIG. 3 regarding the spatial relationship between treatment zones 120 and contaminated region 100, it is within the scope of the present disclosure that first treatment zone 302 and second treatment zone 12 may include and/or define any suitable relative spatial relationship that provides for supply of both first bioremediation formulation 300 and second bioremediation formulation 10 to a given portion of contaminated region 100. As an illustrative, non-exclusive example, and as shown in FIG. 4, first treatment zone 300 may contain, surround, be completely coextensive with, and/or otherwise encompass second treatment zone 12.

As another illustrative, non-exclusive example, second treatment zone 12 may contain, surround, be completely coextensive with, and/or otherwise encompass first treatment zone 302. As yet another illustrative, non-exclusive example, first treatment zone 302 may be partially coextensive with second treatment zone 12. As another illustrative, non-exclusive example, first treatment zone 302 and second treatment zone 12 may initially define separate portions of subsurface region 160. However, at a later time and upon diffusion and/or flow of first bioremediation formulation 300 and/or second bioremediation formulation 10 within subsurface region 160, the first treatment zone and the second treatment zone may be partially and/or completely coextensive within the subsurface region.

FIGS. 5-6 provide illustrative, non-exclusive examples of methods according to the present disclosure that include supplying one or more bioremediation formulations to one or more treatment zones. Any of the systems, compositions, and/or methods that are disclosed herein with reference to FIGS. 1-4 may be utilized with any of the methods of FIGS. 5-6 without departing from the scope of the present disclosure.

As an illustrative, non-exclusive example, the second bioremediation formulation of FIGS. 5-6 may include and/or be second bioremediation formulation 10. As another illustrative, non-exclusive example, the first bioremediation formulation of FIG. 6 may include and/or be first bioremediation formulation 300. As yet another illustrative, non-exclusive example, the treatment zone, first treatment zone, and/or second treatment zone of FIGS. 5-6 may include and/or be treatment zone 120, first treatment zone 302, and/or second treatment zone 12, respectively, of FIGS. 3-4.

FIG. 5 provides illustrative, non-exclusive examples of methods 200 of supplying second bioremediation formulation 10 to a treatment zone 120. Methods 200 may include identifying a contaminated region at 210 and include estimating a mass of contaminant contained within the contaminated region at 220. Methods 200 also may include determining a desired composition of a second bioremediation formulation 10 at 230 and include supplying the second bioremediation formulation to a treatment zone at 240. Methods 200 further may include supplying supplemental materials to the treatment zone at 250 and/or modifying the treatment zone environment at 260.

Identifying the contaminated region at 210 may include the use of any suitable method, procedure, detector, test, monitor, historical information, and/or observation to identify a contaminated region 100. It is within the scope of the present disclosure that identifying the contaminated region at 210 may include at least identifying the general location of the contaminated region.

However, it is also within the scope of the present disclosure that identifying the contaminated region also may include testing to determine the nature of the contaminants that are present within the contaminated region, the chemical composition of the contaminants that are present within the contaminated region, the extent of the contaminated region, the nature of the materials contained within the contaminated region, the mass of competing electron donors that may be present within the contaminated region, the volume of the contaminated region, the surface area of the contaminated region, the depth of the contaminated region, the geological conditions of the contaminated region, the hydrogeological conditions of the contaminated region, the soil type within the contaminated region, the organic content within the contaminated region, the contaminant mobility within the contaminated region, the groundwater flow direction within the contaminated region, the groundwater flow velocity within the contaminated region, the background, or native, electron acceptor concentration within the contaminated region, and/or the identity of and/or the metabolic processes utilized by microorganisms 104 that are present within the contaminated region. It is further within the scope of the present disclosure that identifying the contaminated region may include determining any suitable characteristic and/or property of the contaminated region, including the pH of the contaminated region, the oxygen content of the contaminated region, the water content of the contaminated region, the permeability of the contaminated region, the structure of the native strata contained within the contaminated region, the affinity of contaminant 102 for the native strata contained within the contaminated region, the mobility of contaminant 102 within the contaminated region, and/or the mobility and/or potential mobility of one or more components of second bioremediation formulation 10 within the contaminated region.

Estimating the mass of contaminant contained within the contaminated region at 220 may include utilizing any suitable and/or available information to estimate, approximate, or measure the mass of contaminant contained within the contaminated region. This may include the use of any of the information about the contaminated region that is discussed herein and may further include measuring a concentration, mass, and/or amount of contaminant in one or more portions of, and/or samples that are taken from, the contaminated region, calculating the mass of contaminant utilizing one or more partitioning coefficients, measuring a mass of organic carbon in the contaminated region, and/or knowledge of a known mass of contaminant that may have been released into the contaminated region.

It is within the scope of the present disclosure that the contaminated region may include a single contaminant or a plurality of contaminants. When the contaminated region includes a single contaminant, estimating the mass of contaminant contained within the contaminated region may include estimating the mass of the single contaminant. When the contaminated region includes a plurality of contaminants, estimating the mass of contaminant contained within the contaminated region may include estimating the total mass of contaminant and/or estimating the mass of one or more individual contaminants contained within the contaminated region.

Determining the second bioremediation formulation composition at 230 may include the use of any suitable criteria to determine a suitable second bioremediation formulation 10 for use in a given treatment zone. As an illustrative, non-exclusive example, this may include selecting, or determining, the second bioremediation formulation composition based at least in part on at least one of a characteristic of the treatment zone, a characteristic of the contaminated region, a characteristic of the contaminant, a mobility of the second bioremediation formulation within the treatment zone, and/or a characteristic of the native microbe population. Illustrative, non-exclusive examples of characteristics of the contaminated region may include any suitable characteristic determined when identifying the contaminated region at 210.

Illustrative, non-exclusive examples of characteristics of the contaminant may include any suitable characteristic of the contaminant, including the characteristics discussed herein. Illustrative, non-exclusive examples of characteristics of the native microbe population include any of the characteristics disclosed herein, including the identity of one or more microbes included in the native microbe population, the metabolic processes performed by one or more microbes included in the native microbe population, a rate at which one or more contaminants may be consumed by one or more microbes present in the native microbe population, and/or target environmental conditions for improved growth and/or metabolic functioning of one or more microbes included in the native microbe population.

Supplying the second bioremediation formulation to the treatment zone at 240 may include supplying a mass of the second bioremediation formulation to one or more treatment zones. It is within the scope of the present disclosure that supplying the second bioremediation formulation to the treatment zone may include supplying the second bioremediation formulation based at least in part on the mass of contaminant within the contaminated region as estimated at 220.

As an illustrative, non-exclusive example, and as discussed in more detail herein, this may include supplying a mass of second bioremediation formulation that is calculated based at least in part on the calculated mass of contaminant. As another illustrative, non-exclusive example, this may include supplying a mass of second bioremediation formulation such that, subsequent to consumption of the contaminant by the microorganisms, less than 30%, less than 25%, less than 20%, less than 15%, less than 10%, less than 5%, less than 2.5%, less than 1%, or less than 0.5% of the second bioremediation formulation, and/or of any suitable component thereof, remains within the treatment zone. As another illustrative, non-exclusive example, the supplying may include determining a hydrogen equivalent for the contaminant, each contaminant of the plurality of contaminants, and/or the competing electron donors that may be present within the contaminated region and/or the treatment zone, calculating a total hydrogen equivalent based thereon, and/or calculating the mass of second bioremediation formulation to be provided to the treatment zone based, at least in part, on the calculated total hydrogen equivalent of the contaminant, or plurality of contaminants.

As discussed in more detail herein, supplying the second bioremediation formulation to the treatment zone at 240 may include supplying the second bioremediation formulation in any suitable form, illustrative, non-exclusive examples of which include supplying the second bioremediation formulation in an aqueous solution and supplying the second bioremediation formulation as a dry bioremediation formulation. As discussed in more detail herein, when the second bioremediation formulation is supplied to the treatment zone as an aqueous solution, the second bioremediation formulation may be injected into the treatment zone using any suitable direct push technology, lance injection technique, push probe, monitoring well, and/or infiltration gallery. Similarly, and when the second bioremediation formulation is supplied to the treatment zone as a dry bioremediation formulation, the second bioremediation formulation may be applied to and/or mixed with the materials that comprise the contaminated region, such as the contaminated soil within the contaminated region.

It is within the scope of the present disclosure that supplying the second bioremediation formulation to the treatment zone may include contacting the second bioremediation formulation with the contaminant, surrounding at least a portion of the contaminated region with the second bioremediation formulation, and/or flowing the second bioremediation formulation into the contaminated region. As an illustrative, non-exclusive example, and as discussed in more detail herein, flowing the second bioremediation formulation into the contaminated region may include producing groundwater, mixing the second bioremediation formulation with the produced groundwater to produce an aqueous second bioremediation formulation, and supplying the aqueous second bioremediation formulation to the treatment zone with the produced, or recirculated, groundwater.

It is also within the scope of the present disclosure that supplying the second bioremediation formulation to the treatment zone may include supplying the second bioremediation formulation at any suitable rate and/or using any suitable process. As an illustrative, non-exclusive example, and when the contaminated region includes a high flow rate aquifer, the supplying may include repeatedly and/or periodically supplying the second bioremediation formulation to the treatment zone. The periodically supplying may decrease a potential for the second bioremediation formulation to flow out of the contaminated region and/or provide time for the microbes that are present within the treatment zone to utilize the second bioremediation formulation during their metabolic process, thus increasing the biomass of microbes that are present within the treatment zone.

Supplying supplemental material to the treatment zone at 250 may include supplying any suitable material to complement and/or in addition to the second bioremediation formulation. As an illustrative, non-exclusive example, this may include providing an air stream to the treatment zone. As another illustrative, non-exclusive example, this may include providing one or more chemical oxidants to the treatment zone to chemically oxidize at least a portion of the contaminants contained within the contaminated region.

Modifying the treatment zone environment at 260 may include the use of any suitable material, method, and/or process to modify the treatment zone environment and/or promote the anaerobic microbial bioremediation of contaminants contained therein. As an illustrative, non-exclusive example, this may include at least one of creating an environment in which the second bioremediation formulation is consumed as an oxidant by the microbes present within the treatment zone, creating an environment in which the contaminant is consumed during anaerobic microbial respiration, and/or creating an environment in which the contaminant is oxidized during the anaerobic microbial respiration. Illustrative, non-exclusive examples of modifying the treatment zone environment include changing the pH of the treatment zone, changing the temperature of the treatment zone, changing the oxygen content of the treatment zone, changing the concentration of one or more chemical compositions or elements within the treatment zone, changing the flow characteristics of fluids contained within the treatment zone, changing the permeability of at least a portion of the treatment zone, and/or changing the identity and/or concentration of microbes present within the treatment zone.

FIG. 6 is a flowchart depicting methods 400 according to the present disclosure of decreasing a concentration of a contaminant that is contained within a contaminated region, which also may be referred to herein as bioremediation of the contaminated soil and/or bioremediation methods. Methods 400 include supplying a first bioremediation formulation 300 to a first treatment zone that is associated with the contaminated region at 410 and supplying a second bioremediation formulation 10 to a second treatment zone that is associated with the contaminated region at 440. Methods 400 optionally also may include forming an application site at 405, waiting for a treatment time at 420, fluidly isolating a portion of the application site at 435, supplying bacteria to the contaminated region at 445, supplying a surfactant to the contaminated region at 450, repeating the method at 460, and/or backfilling the application site at 470.

Supplying the first bioremediation formulation at 410, supplying the second bioremediation formulation at 440, supplying bacteria at 445, and/or supplying the surfactant at 450 may include supplying with any suitable supply technique and/or at any suitable supply pressure. As illustrative, non-exclusive examples, the supply pressure may be at least 10 kilopascals (kPa), at least 20 kPa, at least 30 kPa, at least 40 kPa, at least 50 kPa, at least 60 kPa, at least 70 kPa, at least 80 kPa, at least 90 kPa, at least 100 kPa, at least 150 kPa, at least 200 kPa, at least 250 kPa, at least 300 kPa, at least 500 kPa, at least 750 kPa, at least 1 megapascal (MPa), at least 2 MPa, at least 4 MPa, at least 6 MPa, at least 8 MPa, at least 10 MPa, or at least 15 MPa. Additionally or alternatively, the supply pressure may be less than 25 MPa, less than 20 MPa, less than 15 MPa, less than 10 MPa, less than 8 MPa, less than 6 MPa, less than 4 MPa, less than 2 MPa, less than 1 MPa, less than 750 kPa, less than 500 kPa, less than 300 kPa, less than 250 kPa, less than 200 kPa, less than 150 kPa, or less than 100 kPa.

Illustrative, non-exclusive examples of supply techniques that may be utilized with the systems and methods according to the present disclosure include direct push injection, infiltration, and/or direct injection. Direct push injection includes injecting the first bioremediation formulation and injecting the second bioremediation formulation into a common borehole, such as through the use of high-pressure lance injection, a water knife, and/or push probes, at relatively higher pressures, such as pressures in the range of 300 kPa to 20 MPa. Infiltration includes supplying the first bioremediation formulation and the second bioremediation formulation to a portion of the subsurface region that is above the water table, such as through the use of horizontal slotted piping and/or shallow wells at relatively lower pressures, such as pressures in the range of 10-200 kPa. Direct injection includes supplying the first bioremediation formulation and the second bioremediation formulation to the saturated zone using groundwater wells at relatively lower pressures, such as pressures in the range of 10-200 kPa.

Forming the application site at 405 may include forming any suitable application site within the contaminated region. The application site may be utilized to supply any suitable material, such as the first bioremediation formulation, the second bioremediation formulation, the bacteria, and/or the surfactant to the first treatment zone, the second treatment zone, and/or any other suitable portion of the contaminated region.

As illustrative, non-exclusive examples, and when the bioremediation is performed in situ, forming the application site may include forming any suitable borehole and/or well at any suitable contaminated site, wherein the borehole and/or well may extend near and/or within the contaminated region. As another illustrative, non-exclusive example, and when the bioremediation is performed ex situ, forming the application site may include excavating and/or otherwise removing the contaminated region from the contaminated site and locating the contaminated region at any suitable treatment site, where at least a portion of the bioremediation of the contaminant that is contained within the contaminated region may be performed.

Supplying the first bioremediation formulation at 410 may include supplying any suitable bioremediation formulation to the first treatment zone. As illustrative, non-exclusive examples, the supplying at 410 may include supplying first bioremediation formulation 300 that is disclosed herein to the first treatment zone and/or supplying an aqueous bioremediation formulation solution that includes first bioremediation formulation 300 to the first treatment zone.

Waiting for a treatment time at 420 may include waiting for any suitable period of time between supplying the first bioremediation formulation and supplying the second bioremediation formulation. As an illustrative, non-exclusive example, methods 400 may include supplying the first bioremediation formulation at 410 and waiting for the treatment time prior to supplying the second bioremediation formulation at 440 (i.e., supplying the first bioremediation formulation prior to supplying the second bioremediation formulation). This treatment time may provide a period of time during which the first bioremediation formulation may react with, modify, change, destabilize, decrease a concentration of, and/or otherwise prepare the contaminant and/or the contaminated region for the supply of the second bioremediation formulation at 440. This may improve a rate of removal of the contaminant by the second bioremediation formulation and/or provide for an overall contaminant removal that is greater than what might be accomplished using only the supplying at 410 or the supplying at 440.

It is within the scope of the present disclosure that the treatment time may include any suitable treatment time. As illustrative, non-exclusive examples, the treatment time may be at least 1 hour (h), at least 2 h, at least 4 h, at least 6 h, at least 8 h, at least 10 h, at least 12 h, at least 16 h, at least 20 h, at least 1 day, at least 2 days, at least 3 days, at least 4 days, at least 5 days, at least 6 days, at least 8 days, at least 10 days, at least 12 days, at least 14 days, at least 16 days, at least 20 days, at least 25 days, at least 30 days, at least 40 days, at least 50 days, at least 60 days, at least 70 days, at least 80 days, or at least 90 days. Additionally or alternatively, the treatment time also may be less than 100 days, less than 90 days, less than 80 days, less than 70 days, less than 60 days, less than 50 days, less than 40 days, less than 30 days, less than 25 days, less than 20 days, less than 16 days, less than 14 days, less than 12 days, less than 10 days, less than 8 days, less than 6 days, less than 5 days, less than 4 days, less than 3 days, less than 2 days, less than 1 day, less than 20 h, less than 16 h, less than 12 h, less than 10 h, less than 8 h, less than 6 h, less than 4 h, less than 2 h, or less than 1 h.

Fluidly isolating a portion of the application site at 435 may include fluidly isolating a first portion of the application site from a second portion of the application site based upon any suitable criteria. As an illustrative, non-exclusive example, the first portion of the application site may extend within the first treatment zone, the second portion of the application site may extend within the second treatment zone, and the fluidly isolating may include fluidly isolating the first portion of the application site from the second portion of the application site subsequent to supplying the first bioremediation formulation at 410 but prior to supplying the second bioremediation formulation at 440. This may provide for supplying the first bioremediation formulation and the second bioremediation formulation such that the first treatment zone is not completely coextensive with the second treatment zone, as discussed in more detail herein with reference to FIG. 4.

The fluidly isolating may be accomplished with any suitable system and/or method. As illustrative, non-exclusive examples, the fluidly isolating may include supplying and/or locating a packer, a plug, and/or hydrated bentonite within the application site and/or within a borehole, well, and/or infiltration gallery thereof.

Supplying the second bioremediation formulation at 440 may include supplying any suitable second bioremediation formulation to the second treatment zone. As illustrative, non-exclusive examples, the supplying at 440 may include supplying second bioremediation formulation 10 that is disclosed herein to the second treatment zone and/or supplying an aqueous bioremediation formulation solution that includes second bioremediation formulation 10 to the second treatment zone.

This may include supplying the second bioremediation formulation using methods 200 or any suitable portion thereof, which are discussed in more detail herein with reference to FIG. 5. When the supplying at 440 includes supplying with methods 200, it is within the scope of the present disclosure that any individual step of methods 200 may be performed at any suitable time relative to any individual step of methods 400. As an illustrative, non-exclusive example, steps 210, 220, and/or 230 of methods 200 may be performed prior to beginning methods 400 and/or prior to the supplying at 410.

It is within the scope of the present disclosure that the supplying at 440 may be performed at any suitable time. As an illustrative, non-exclusive example, the supplying at 440 may include supplying after the waiting at 420. As another illustrative, non-exclusive example, the supplying at 440 may include supplying immediately after the supplying at 410.

Supplying bacteria to the contaminated region at 445 may include supplying any suitable bacteria species, illustrative, non-exclusive examples of which are discussed in more detail herein. The supplied bacteria may supplement any native bacteria that may be present within the contaminated region, participate in the bioremediation of the contaminant, and/or increase the overall rate of contaminant removal from the contaminated region. Supplying the bacteria at 445 may include supplying the bacteria to any suitable portion of the contaminated region, such as to the first treatment zone and/or to the second treatment zone.

It is within the scope of the present disclosure that supplying the bacteria at 445 may be performed at any suitable time relative to supplying the first bioremediation formulation at 410 and supplying the second bioremediation formulation at 440. As illustrative, non-exclusive examples, supplying the bacteria may be performed separately from or concurrently with supplying the first bioremediation formulation and/or supplying the second bioremediation formulation. As another illustrative, non-exclusive example, supplying the bacteria may include supplying the bacteria subsequent to supplying the first bioremediation formulation and prior to supplying the second bioremediation formulation. As yet another illustrative, non-exclusive example, supplying the bacteria may include supplying the bacteria subsequent to supplying both the first bioremediation formulation and the second bioremediation formulation. As another illustrative, non-exclusive example, supplying the bacteria may include supplying the bacteria at least 0.5 days, at least 1 day, at least 2 days, at least 3 days, at least 4 days, at least 5 days, at least 10 days, or at least 15 days after supplying the first bioremediation formulation and/or after supplying the second bioremediation formulation.

Supplying the surfactant to the contaminated region at 450 may include supplying any suitable surfactant material to the contaminated region, to the first treatment zone, and/or to the second treatment zone. The surfactant may increase a solubility of, increase an availability of, and/or modify an activity of the first bioremediation formulation, the second bioremediation formulation, and/or the contaminant, thereby increasing the overall efficiency of contaminant removal. It is within the scope of the present disclosure that the surfactant may be supplied concurrently with the second bioremediation formulation, that the surfactant may be mixed with the second bioremediation formulation prior to supplying the second bioremediation formulation, and/or that the surfactant may form a portion of the second bioremediation formulation.

Repeating the method at 460 may include repeating any suitable portion of method 400 to supply, or re-supply, any suitable first bioremediation formulation, bacteria, second bioremediation formulation, and/or surfactant to the contaminated region. As an illustrative, non-exclusive example, the repeating may include periodically supplying the first bioremediation formulation to the contaminated region and subsequently supplying the second bioremediation formulation to the contaminated region after each periodic supply of the first bioremediation formulation. Additionally or alternatively, the repeating may include periodically supplying the first bioremediation formulation to the contaminated region without subsequently supplying the second bioremediation formulation after each instance of supplying the first bioremediation formulation. Additionally or alternatively, the repeating may include periodically supplying the second bioremediation formulation to the contaminated region without first repeating the supplying of the first bioremediation formulation prior to each instance of supplying the second bioremediation formulation.

Backfilling the application site at 470 may include backfilling any suitable borehole, well, and/or infiltration gallery that functions as the application site with any suitable sealing material, illustrative, non-exclusive examples of which are disclosed herein. The backfilling may be performed subsequent to a remainder of the method, thereby sealing the application site and/or occluding a fluid flow therein.

The following embodiments describe more specific but still illustrative, non-exclusive examples of methods 400 according to the present disclosure. These embodiments include both in situ embodiments and ex situ embodiments. Any of the systems and/or methods disclosed herein may be utilized with any of the given embodiments without departing from the scope of the present disclosure. Similarly, any portion of any of the given embodiments may be utilized with any of the systems and/or methods disclosed herein without departing from the scope of the present disclosure In in situ embodiments of methods 400, the first bioremediation formulation 300 and the second bioremediation formulation 10 may be provided to a contaminated site without substantial disturbance of the contaminated region and/or removal of a material that comprises the contaminated region from the contaminated site. The contaminated region may include a subsurface region that includes the contaminant and the contaminant may be located in the vadose zone of the subsurface region, the smear zone of the subsurface region, and/or the saturated zone of the subsurface region. Furthermore, the first treatment zone and/or the second treatment zone may include any suitable portion of the vadose zone, the smear zone, and/or the saturated zone.

In ex situ embodiments of methods 400, the material that comprises the contaminated region may be removed from the contaminated site and/or substantially disturbed from the contaminated site during at least a portion of the method. Thus, the first bioremediation formulation and/or the second bioremediation formulation may be provided to the contaminated region at a location that is different from the contaminated site and/or the contaminated region may be excavated and/or otherwise disturbed and/or removed from the contaminated site prior to supply of the first bioremediation formulation and/or the second bioremediation formulation thereto.

In Situ Direct Push Injection Embodiment

As an illustrative, non-exclusive example, the systems and methods according to the present disclosure may include in situ direct push injection of the first bioremediation formulation and the second bioremediation formulation into the first treatment zone and the second treatment zone, respectively. This may include supplying the first bioremediation formulation at 410 and subsequently supplying the second bioremediation formulation at 440 to a borehole that extend from the surface region and within the contaminated region.

The borehole may be formed in any suitable manner, illustrative, non-exclusive examples of which include forming the borehole with a high pressure lance, a water knife, and/or a push probe. In addition, the first bioremediation formulation and/or the second bioremediation formulation may be supplied at any suitable supply pressure, such as supply pressures of 300 kPa to 20 MPa.

The first bioremediation formulation may be supplied to the first treatment zone in a dilute aqueous solution of the first bioremediation formulation that includes 0.03-0.3 wt % of the first bioremediation formulation in water, such as municipal tap water, ground water, and/or surface water. Furthermore, the dilute aqueous solution of the first bioremediation formulation may be supplied at any suitable application rate to any suitable portion of the borehole, such as to a portion of the borehole that extends between, or within, the surface region and the total treatment depth, wherein the total treatment depth is defined within the saturated zone or the vadose zone.

As illustrative, non-exclusive examples, the dilute aqueous solution of the first bioremediation formulation may be supplied along a first length of the borehole at an application rate of at least 1 liter (L), at least 2 L, at least 3 L, at least 4 L, at least 5 L, at least 6 L, at least 8 L, at least 10 L, or at least 12 L of the dilute aqueous solution of the first bioremediation formulation per meter of the first length of the borehole. Additionally or alternatively, the dilute aqueous solution of the first bioremediation formulation may be supplied along the first length of the borehole at an application rate of less than 15 L, less than 14 L, less than 12 L, less than 10 L, less than 8 L, less than 6 L, less than 5 L, less than 4 L, less than 3 L, or less than 2 L of the dilute aqueous solution of the first bioremediation formulation per meter of the first length of the borehole.

Similarly, the second bioremediation formulation may be supplied to the second treatment zone in any suitable manner. As an illustrative, non-exclusive example, the second bioremediation formulation may be mechanically mixed with a portion of the contaminated region that includes the second treatment zone, such as through tilling and/or excavation, to distribute the second bioremediation formulation within the second treatment zone.

As another illustrative, non-exclusive example, and similar to the dilute aqueous solution of the first bioremediation formulation, an aqueous solution of the second bioremediation formulation may be injected along a second length of the borehole, such as to a portion of the borehole that extends between, or within, the smear zone and the total treatment depth, to a portion of the borehole that extends between, or within, the surface region and the total treatment depth, and/or to a portion of the borehole that extends between, or within, the smear zone and the saturated zone. When the second length of the borehole is different from the first length of the borehole, the fluidly isolating at 435 may be utilized to provide for the difference therebetween.

This may include injecting the aqueous solution of the second bioremediation formulation at any suitable application rate. As an illustrative, non-exclusive example, the aqueous solution of the second bioremediation formulation may be injected at an application rate that provides for injection of at least 1 kilogram (kg), at least 2 kg, at least 3 kg, at least 4 kg, at least 5 kg, at least 6 kg, at least 8 kg, at least 10 kg, at least 12 kg, at least 14 kg, at least 16 kg, at least 18 kg, at least 20 kg, at least 22 kg, at least 24 kg, at least 26 kg, or at least 28 kg of the second bioremediation formulation per meter of the second length of the borehole. Additionally or alternatively, the aqueous solution of the second bioremediation formulation also may be injected at an application rate that provides for injection of less than 30 kg, less than 28 kg, less than 26 kg, less than 24 kg, less than 22 kg, less than 20 kg, less than 18 kg, less than 16 kg, less than 14 kg, less than 12 kg, less than 10 kg, less than 8 kg, less than 6 kg, less than 4 kg, or less than 2 kg of the second bioremediation formulation per meter of the second length of the borehole.

It is within the scope of the present disclosure that the borehole may be a first borehole and that repeating the method at 460 may include repeating the method in a second borehole that is different from the first borehole. This may include forming the first borehole and/or forming the second borehole at 405. This process may be repeated any suitable number of times to produce a plurality of boreholes and/or to supply at least the first bioremediation formulation and the second bioremediation formulation to the plurality of boreholes. When methods 400 include supplying at least the first bioremediation formulation and the second bioremediation formulation to the plurality of boreholes, it is within the scope of the present disclosure that a number of boreholes in the plurality of boreholes and/or a spacing among the plurality of boreholes may be determined and/or selected based, at least in part, on a total mass of contaminant within the contaminated region, a concentration of contaminant within a given portion of the contaminated region that is associated with a given borehole, a mobility of the first bioremediation formulation and/or the second bioremediation formulation within the contaminated region, and/or an extent, size, and/or volume of the contaminated region.

In Situ Infiltration Embodiment

As another illustrative, non-exclusive example, the systems and methods according to the present disclosure may include in situ infiltration of the first bioremediation formulation 300 and the second bioremediation formulation 10 into the first treatment zone and the second treatment zone, respectively. This may include supplying a dilute aqueous solution of the first bioremediation formulation that includes, for example, 0.01-0.3 wt % of the first bioremediation formulation in water, to the vadose zone at 410. Subsequent to the supplying at 410, the dilute aqueous solution of the first bioremediation formulation may flow through the subsurface region and to the saturated zone. As an illustrative, non-exclusive example, the supplying at 410 may include supplying the dilute aqueous solution of the first bioremediation formulation to an infiltration gallery, such as a horizontal slotted pipe and/or a shallow well, that is present within the vadose zone. It is within the scope of the present disclosure that the supplying at 410 may include supplying the dilute aqueous solution of the first bioremediation formulation to saturate a portion of the contaminated region that extends between the vadose zone and the saturated zone with the dilute aqueous solution of the first bioremediation formulation.

Subsequent to the supplying at 410, an aqueous solution of the second bioremediation formulation may be supplied to the infiltration gallery at 440 to saturate the portion of the contaminated region that extends between the vadose zone and the saturated zone with the aqueous solution of the second bioremediation formulation. The aqueous solution of the second bioremediation formulation may include any suitable concentration and/or proportion of the second bioremediation formulation in water, illustrative, non-exclusive examples of which are disclosed herein. As additional illustrative, non-exclusive examples, the second bioremediation formulation may comprise at least 0.01 wt %, at least 0.02 wt %, at least 0.05 wt %, at least 0.1 wt %, at least 0.5 wt %, at least 1 wt %, at least 2.5 wt %, at least 5 wt %, at least 7.5 wt %, or at least 10 wt % of the aqueous solution of the second bioremediation formulation. Additionally or alternatively, the second bioremediation formulation also may comprise less than 15 wt %, less than 12.5 wt %, less than 10 wt %, less than 7.5 wt %, less than 5 wt %, less than 2.5 wt %, less than 1 wt %, or less than 0.5 wt % of the aqueous solution of the second bioremediation formulation.

In Situ Direct Injection Embodiment

As another illustrative, non-exclusive example, the systems and methods according to the present disclosure may include in situ direct injection of the first bioremediation formulation 300 and the second bioremediation formulation 10 into the first treatment zone and the second treatment zone, respectively. This may include supplying the first bioremediation formulation to a groundwater well that extends from the surface region and within the contaminated region at 410 and supplying the second bioremediation formulation to the groundwater well at 420.

Supplying the first bioremediation formulation at 410 may include supplying any suitable aqueous solution of the first bioremediation formulation in water, illustrative, non-exclusive examples of which are discussed in more detail herein, to the groundwater well. Supplying the second bioremediation formulation at 440 may include supplying an aqueous solution of the second bioremediation formulation, illustrative, non-exclusive examples of which are discussed in more detail herein, to the groundwater well. As additional illustrative, non-exclusive examples, the second bioremediation formulation may comprise at least 0.1 wt %, at least 0.25 wt %, at least 0.5 wt %, at least 1 wt %, at least 2 wt %, at least 3 wt %, at least 4 wt %, at least 5 wt %, at least 6 wt %, at least 8 wt %, at least 10 wt %, at least 15 wt %, or at least 20 wt % of the aqueous solution of the second bioremediation formulation. Additionally or alternatively, the second bioremediation formulation also may comprise less than 30 wt %, less than 25 wt %, less than 20 wt %, less than 15 wt %, less than 10 wt %, less than 8 wt %, less than 7 wt %, less than 6 wt %, less than 5 wt %, less than 4 wt %, less than 3 wt %, less than 2 wt %, or less than 1 wt % of the aqueous solution of the second bioremediation formulation.

It is within the scope of the present disclosure that the groundwater well may be a first groundwater well and that the contaminated site also may be associated with a second groundwater well. Thus, methods 400 further may include producing groundwater from the second groundwater well, recirculating the groundwater from the second groundwater well to the first groundwater well, and injecting the produced groundwater into the first groundwater well concurrently with the supplying at 410 and/or the supplying at 440. Methods 400 further may include mixing the first bioremediation formulation with the produced groundwater to produce the aqueous solution of the first bioremediation formulation and/or mixing the second bioremediation formulation with the produced groundwater to produce the aqueous solution of the second bioremediation formulation prior to the recirculating to accomplish the supplying at 410 and/or the supplying at 440.

It is also within the scope of the present disclosure that the supplying at 410 and/or the supplying at 440 may include periodically supplying the first bioremediation formulation to the first treatment zone and subsequently supplying the second bioremediation formulation to the second treatment zone. Thus, the repeating at 460 may include supplying the first bioremediation formulation to the first treatment zone a plurality of times and subsequently supplying the second bioremediation formulation after each periodic supply of the first bioremediation formulation.

Ex Situ Embodiments

As other illustrative, non-exclusive examples, the systems and methods according to the present disclosure may include ex situ bioremediation of the contaminated region to remove contaminants that are contained therein. As an illustrative, non-exclusive example, the contaminated region may include a soil sample that has been excavated and/or otherwise removed from the contaminated site, and any of the methods disclosed herein may be utilized to remove contaminants from the excavated soil sample. Additionally or alternatively, supplying the first bioremediation formulation at 410 and/or supplying the second bioremediation formulation at 440 may include spraying an aqueous solution of the first bioremediation formulation and/or an aqueous solution of the second bioremediation formulation, illustrative, non-exclusive examples of which are disclosed herein, onto the soil sample. Subsequent to the spraying, the methods also may include mechanically mixing the aqueous solution of the first bioremediation formulation and/or the aqueous solution of the second bioremediation formulation with the soil sample, such as by tilling and/or rotation of the soil sample.

It is within the scope of the present disclosure that methods 400 further may include excavating the soil sample from the contaminated site to form the application site at 405. When the methods include excavating the soil sample from the contaminated site, the excavating may be performed prior to both the supplying at 410 and the supplying at 440, subsequent to the supplying at 410 but prior to the supplying at 440, and/or subsequent to both the supplying at 410 and the supplying at 440. Thus, it is within the scope of the present disclosure that a portion, or all, of methods 400 may be performed in situ, or within the contaminated site, while a portion, or all, of methods 400 may be performed ex situ, or at a location that is removed and/or disturbed from the contaminated site.

Illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. A bioremediation formulation configured to provide at least a portion of the oxidants and nutrients that are consumed by a native microbe population during anaerobic respiration and to promote anaerobic oxidative bioremediation of a contaminant contained within a treatment zone that is associated with a contaminated region, the bioremediation formulation comprising:

a high-mobility oxidant, wherein the high-mobility oxidant has a high-mobility oxidant diffusion constant when present within the treatment zone;

a low-mobility oxidant, wherein the low-mobility oxidant has a low-mobility oxidant diffusion constant when present within the treatment zone, and further wherein the low-mobility oxidant diffusion constant is less than the high-mobility oxidant diffusion constant; and a nutrient material.

A2. The bioremediation formulation of paragraph A1, wherein the bioremediation formulation further includes a mid-mobility oxidant, wherein the mid-mobility oxidant has a mid-mobility oxidant diffusion constant when present within the treatment zone, wherein the mid-mobility oxidant diffusion constant is less than the high-mobility oxidant diffusion constant, and further wherein the mid-mobility oxidant diffusion constant is greater than the low-mobility oxidant diffusion constant.

A3. The bioremediation formulation of paragraph A2, wherein the mid-mobility oxidant comprises 1-70 wt % of the bioremediation formulation, optionally including 1-65 wt %, 1-60 wt %, 1-40 wt %, 1-30 wt %, 10-60 wt %, 20-60 wt %, 10-30 wt %, 5-10 wt %, 5-15 wt %, 10-20 wt %, 20-30 wt %, 20-40 wt %, or 25-35 wt % of the bioremediation formulation, and further optionally wherein the wt % includes a wt % of the active components of the bioremediation formulation.

A4. The bioremediation formulation of any of paragraphs A2-A3, wherein the mid-mobility oxidant includes a sulfate salt.

A5. The bioremediation formulation of paragraph A4, wherein the sulfate salt includes at least one of calcium sulfate, magnesium sulfate, and ammonium sulfate.

A6. The bioremediation formulation of any of paragraphs A1-A5, wherein the nutrient material includes at least a first complex sugar.

A7. The bioremediation formulation of paragraph A6, wherein the at least a first complex sugar includes at least one of an α-bonded polysaccharide, a starch, an amylopectin, a β-bonded polysaccharide, cellulose, a modified β-bonded polysaccharide, chitin, carboxymethylcellulose, ribose, and a glycoprotein.

A8. The bioremediation formulation of any of paragraphs A6-A7, wherein the at least a first complex sugar comprises 1-20 wt % of the bioremediation formulation, optionally comprising 2-18 wt %, 3-17 wt %, 5-15 wt %, 7-12 wt %, 5-10 wt %, or 10-15 wt % of the bioremediation formulation, and further optionally wherein the wt % includes a wt % of the active components of the bioremediation formulation.

A9. The bioremediation formulation of any of paragraphs A1-A8, wherein the nutrient material includes brewer's yeast.

A10. The bioremediation formulation of any of paragraphs A1-A9, wherein the brewer's yeast comprises 1-20 wt % of the bioremediation formulation, optionally comprising 2-18 wt %, 3-17 wt %, 5-15 wt %, 7-12 wt %, 5-10 wt %, or 10-15 wt % of the bioremediation formulation, and further optionally wherein the wt % includes a wt % of the active components of the bioremediation formulation.

A11. The bioremediation formulation of any of paragraphs A1-A10, wherein the bioremediation formulation further includes at least a first additional component.

A12. The bioremediation formulation of paragraph A11, wherein the at least a first additional component includes at least one of an ionic surfactant, a non-ionic surfactant, a co-solvent, and a bio-augmentation species.

A13. The bioremediation formulation of any of paragraphs A1-A12, wherein the high-mobility oxidant comprises 1-50 wt % of the bioremediation formulation, optionally including 1-45 wt %, 1-40 wt %, 10-40 wt %, 10-30 wt %, 5-10 wt %, 5-15 wt %, 10-20 wt %, or 20-30 wt % of the bioremediation formulation, and further optionally wherein the wt % includes a wt % of the active components of the bioremediation formulation.

A14. The bioremediation formulation of any of paragraphs A1-A13, wherein the high-mobility oxidant includes a nitrate salt.

A15. The bioremediation formulation of paragraph A14, wherein the nitrate salt includes at least one of potassium nitrate, sodium nitrate, and magnesium nitrate.

A16. The bioremediation formulation of any of paragraphs A1-A15, wherein the low-mobility oxidant comprises 1-70 wt % of the bioremediation formulation, optionally including 1-65 wt %, 1-60 wt %, 1-40 wt %, 1-30 wt %, 10-60 wt %, 20-60 wt %, 10-30 wt %, 5-10 wt %, 5-15 wt %, 10-20 wt %, 20-30 wt %, 20-40 wt %, or 25-35 wt % of the bioremediation formulation, and further optionally wherein the wt % includes a wt % of the active components of the bioremediation formulation.

A17. The bioremediation formulation of any of paragraphs A1-A16, wherein the low-mobility oxidant includes a sulfate salt.

A18. The bioremediation formulation of paragraph A17, wherein the sulfate salt includes at least one of calcium sulfate, magnesium sulfate, and ammonium sulfate.

A19. The bioremediation formulation of any of paragraphs A1-A18, wherein the bioremediation formulation further includes at least a first phosphate, and optionally wherein the at least a first phosphate includes at least one of diammonium phosphate, ammonium polyphosphate, and tetrapotassium pyrophosphate.

A20. The bioremediation formulation of paragraph A19, wherein the at least a first phosphate comprises 1-40 wt % of the bioremediation formulation, optionally comprising 5-35 wt %, 10-30 wt %, 10-20 wt %, 20-30 wt %, 15-25 wt %, or 18-22 wt % of the bioremediation formulation, and further optionally wherein the wt % includes a wt % of the active components of the bioremediation formulation.

A21. The bioremediation formulation of any of paragraphs A19-A20, wherein a nitrogen to phosphorous ratio in the bioremediation formulation is between 2:1 and 8:1, optionally including nitrogen to phosphorous ratios between 3:1 and 6:1, and further optionally including nitrogen to phosphorous ratios of approximately 3.5:1, 4:1, 4.5:1, 5:1, or 5.5:1.

A22. The bioremediation formulation of any of paragraphs A1-A21, wherein the contaminant includes at least one of a hydrocarbon, a petroleum hydrocarbon, a metal, a partially halogenated solvent, a partially halogenated organic, and vinyl chloride.

A23. The bioremediation formulation of any of paragraphs A1-A22, wherein the native microbe population includes at least one of bacteria, fungi, denitrifiers, sulfate reducers, anaerobic species, facultative anaerobic species, and facultative aerobic species.

B1. A bioremediation formulation configured to provide at least a portion of the oxidants and nutrients that are consumed by a native microbe population during anaerobic respiration and to promote anaerobic oxidative bioremediation of a contaminant contained within a treatment zone that is associated with a contaminated region, the bioremediation formulation comprising:
  a sulfate salt, wherein the sulfate salt comprises 20-60 wt % of the bioremediation formulation, and optionally wherein the wt % includes a wt % of the active components of the bioremediation formulation;
  a nitrate salt, wherein the nitrate salt comprises 10-40 wt % of the bioremediation formulation, and optionally wherein the wt % includes a wt % of the active components of the bioremediation formulation;
  a phosphate salt, wherein the phosphate salt comprises 10-30 wt % of the bioremediation formulation, and optionally wherein the wt % includes a wt % of the active components of the bioremediation formulation;
  a complex sugar, wherein the complex sugar comprises 5-15 wt % of the bioremediation formulation, and optionally wherein the wt % includes a wt % of the active components of the bioremediation formulation; and
  brewer's yeast, wherein the brewer's yeast comprises 5-15 wt % of the bioremediation formulation, and optionally wherein the wt % includes a wt % of the active components of the bioremediation formulation.

C1. A bioremediation formulation configured to provide at least a portion of the oxidants and nutrients that are consumed by a native microbe population during anaerobic respiration and to promote anaerobic oxidative bioremediation of a contaminant contained within a treatment zone that is associated with a contaminated region, the bioremediation formulation consisting essentially of:
  a sulfate salt, wherein the sulfate salt comprises 20-60 wt % of the bioremediation formulation, and optionally wherein the wt % includes a wt % of the active components of the bioremediation formulation;
  a nitrate salt, wherein the nitrate salt comprises 10-40 wt % of the bioremediation formulation, and optionally wherein the wt % includes a wt % of the active components of the bioremediation formulation;
  a phosphate salt, wherein the phosphate salt comprises 10-30 wt % of the bioremediation formulation, and optionally wherein the wt % includes a wt % of the active components of the bioremediation formulation;
  a complex sugar, wherein the complex sugar comprises 5-15 wt % of the bioremediation formulation, and optionally wherein the wt % includes a wt % of the active components of the bioremediation formulation; and
  brewer's yeast, wherein the brewer's yeast comprises 5-15 wt % of the bioremediation formulation, and optionally wherein the wt % includes a wt % of the active components of the bioremediation formulation.

D1. The bioremediation formulation of any of paragraphs B1-C1, wherein the sulfate salt includes calcium sulfate, and optionally wherein the sulfate salt further includes at least one of magnesium sulfate and ammonium sulfate.

D2. The bioremediation formulation of any of paragraphs B1-D1, wherein the nitrate salt includes potassium nitrate, and optionally wherein the nitrate salt further includes at least one of sodium nitrate and magnesium nitrate.

D3. The bioremediation formulation of any of paragraphs B1-D2, wherein the phosphate salt includes at least one of diammonium phosphate, ammonium phosphate, and tetrapotassium pyrophosphate.

D4. The bioremediation formulation of any of paragraphs B1-D3, wherein the complex sugar includes at least one of an α-bonded polysaccharide, a starch, an amylopectin, a β-bonded polysaccharide, cellulose, a modified β-bonded polysaccharide, chitin, carboxymethylcellulose, ribose, and a glycoprotein.

E1. An aqueous bioremediation solution, the solution comprising:
  water; and
  the bioremediation formulation of any of paragraphs A1-D4.

E2. The aqueous bioremediation solution of paragraph E1, wherein the bioremediation formulation comprises 5-65 wt % of the aqueous bioremediation solution, optionally including 5-50 wt %, 5-40 wt %, 5-30 wt %, 5-20 wt %, 5-15 wt %, 5-10 wt %, 10-25 wt %, 10-20 wt %, 10-15 wt %, 11 wt %, 12 wt %, 13 wt %, or 14 wt % of the aqueous bioremediation solution.

F1. An aquifer comprising:
  water;
  a contaminant; and
  the bioremediation formulation of any of paragraphs A1-D4.

F2. The aquifer of paragraph F1, wherein the contaminant includes a hydrocarbon, and further wherein the aquifer includes 0.2-10 kilograms of the bioremediation formulation per kilogram of the contaminant present within the aquifer, optionally wherein the aquifer includes at least 0.2, at least 0.4, at least 0.5, at least 0.6, at least 0.7, at least 0.8, at least 1, at least 1.5, at least 2, at least 2.5, at least 3, at least 3.5, at least 4, at least 4.5, or at least 5 kilograms of the bioremediation formulation for each kilogram of the contaminant present within the aquifer, and further optionally wherein the aquifer includes less than 10, less than 9.5, less than 9, less than 8.5, less than 8, less than 7.5, less than 7, less than 6.5, less than 6, less than 5.5, less than 5, less than 4.5, less than 4, less than 3.5, less than 3, or less than 2.5 kilograms of the bioremediation formulation for each kilogram of the contaminant present within the aquifer.

F3. The aquifer of any of paragraphs F1-F2, wherein the bioremediation formulation is present within at least one of the entire aquifer, a contaminated portion of the aquifer, and a barrier region within the aquifer.

G1. A soil sample comprising:
  a contaminant; and
  the bioremediation formulation of any of paragraphs A1-D4.

G2. The soil sample of paragraph G1, wherein the contaminant includes a hydrocarbon, and further wherein the soil sample includes 0.2-10 kilograms of the bioremediation formulation per kilogram of the contaminant present within the soil sample, optionally wherein the soil sample includes at least 0.2, at least 0.4, at least 0.5, at least 0.6, at least 0.7, at least 0.8, at least 1, at least 1.5, at least 2, at least 2.5, at least 3, at least 3.5, at least 4, at least 4.5, or at least 5 kilograms of the bioremediation formulation for each kilogram of the contaminant present within the soil sample, and further optionally wherein the soil sample includes less than 10, less than 9.5, less than 9, less than 8.5, less than 8, less than 7.5, less than 7, less than 6.5, less than 6, less than 5.5, less than 5, less than 4.5, less than 4, less than 3.5, less than 3, or less than 2.5 kilograms of the bioremediation formulation for each kilogram of the contaminant present within the soil sample.

G3. The soil sample of any of paragraphs G1-G2, wherein the bioremediation formulation is present within the treatment zone, and further wherein the treatment zone includes at least one of the entire soil sample, a contaminated portion of the soil sample, and a barrier region within the soil sample.

H1. A method of supplying an oxidant and nutrients to a native microbe population to promote consumption of a contaminant by anaerobic microbial respiration, wherein the contaminant is contained within a treatment zone that is associated with a contaminated region, the method comprising:

estimating a mass of contaminant present within at least a portion of the contaminated region; and supplying a mass of the bioremediation formulation of any of paragraphs A1-D4 to the treatment zone, wherein the supplying is based at least in part on the estimating, and further wherein the supplying supports the anaerobic oxidative bioremediation of the contaminant.

H2. The method of paragraph H1, wherein the supplying includes supplying between 0.2 and 10 kilograms of bioremediation formulation per kilogram of contaminant present within the portion of the contaminated region, optionally including supplying at least 0.2, at least 0.4, at least 0.5, at least 0.6, at least 0.7, at least 0.8, at least 1, at least 1.5, at least 2, at least 2.5, at least 3, at least 3.5, at least 4, at least 4.5, or at least 5 kilograms of the bioremediation formulation for each kilogram of the contaminant present within the portion of the contaminated region, and further optionally including supplying less than 10, less than 9.5, less than 9, less than 8.5, less than 8, less than 7.5, less than 7, less than 6.5, less than 6, less than 5.5, less than 5, less than 4.5, less than 4, less than 3.5, less than 3, or less than 2.5 kilograms of the bioremediation formulation for each kilogram of the contaminant present within the portion of the contaminated region.

H3. The method of any of paragraphs H1-H2, wherein the method further includes mixing the bioremediation formulation with water to form an aqueous bioremediation solution, wherein the bioremediation formulation comprises 5-65 wt % of the aqueous bioremediation solution, optionally including 5-50 wt %, 5-40 wt %, 5-30 wt %, 5-20 wt %, 5-15 wt %, 5-10 wt %, 10-25 wt %, 10-20 wt %, 10-15 wt %, 11 wt %, 12 wt %, 13 wt %, or 14 wt % of the aqueous bioremediation solution, and further wherein the supplying includes supplying the aqueous bioremediation solution to the treatment zone, and optionally wherein the wt % includes a wt % of the active components of the bioremediation formulation.

H4. The method of paragraph H3, wherein the contaminated region includes an aquifer.

H5. The method of any of paragraphs H1-H4, wherein the method further includes providing a chemical oxidant to the treatment zone and oxidizing the contaminant with the chemical oxidant, and optionally wherein the chemical oxidant is not consumed by the native microbe population.

H6. The method of any of paragraphs H1-H5, wherein the supplying includes mixing the bioremediation formulation with a contaminated soil sample.

H7. The method of any of paragraphs H1-H6, wherein the supplying includes injecting the bioremediation formulation into the treatment zone, and optionally wherein the injecting includes at least one of injecting with a direct push technology, a lance injection technique, a push probe, injecting into a monitoring well, and injecting into an infiltration gallery.

H8. The method of any of paragraphs H1-H7, wherein the supplying includes contacting the bioremediation formulation with the contaminant.

H9. The method of any of paragraphs H1-H8, wherein the supplying includes surrounding at least a portion of the contaminated region with the bioremediation formulation.

H10. The method of any of paragraphs H1-H9, wherein the method further includes producing groundwater from the treatment zone and recirculating the produced groundwater into the treatment zone as recirculated groundwater, and optionally wherein the supplying includes supplying the bioremediation formulation in the recirculated groundwater.

H11. The method of any of paragraphs H1-H10, wherein the method further includes providing air to the treatment zone.

H12. The method of any of paragraphs H1-H11, wherein the method further includes creating an environment in which the bioremediation formulation is consumed as an oxidant to promote anaerobic microbial respiration.

H13. The method of any of paragraphs H1-H12, wherein the method further includes creating an environment in which the contaminant is degraded during anaerobic microbial respiration.

H14. The method of paragraph H13, wherein the method further includes creating an environment in which the contaminant is oxidized during anaerobic microbial respiration.

H15. The method of any of paragraphs H1-H14, wherein the contaminant includes at least one of a hydrocarbon, a petroleum hydrocarbon, a metal, a partially halogenated solvent, a partially halogenated organic, and vinyl chloride.

H16. The method of any of paragraphs H1-H15, wherein the native microbe population includes at least one of bacteria, fungi, denitrifiers, sulfate reducers, anaerobic species, facultative anaerobic species, and facultative aerobic species.

H17. The method of any of paragraphs H1-H16, wherein the method further includes selecting a composition of the bioremediation formulation based on at least one of a characteristic of the contaminated region, a characteristic of the contaminant, and a characteristic of the native microbe population.

H18. The method of any of paragraphs H1-H17, the method further including identifying the contaminated region.

I1. A bioremediation formulation, comprising:
an ion exchange resin.

I2. The bioremediation formulation of paragraph I1, wherein the ion exchange resin is a cationic ion exchange resin.

I3. The bioremediation formulation of any of paragraphs I1-I2, wherein the ion exchange resin includes at least one of a polymeric material, a cross-linked polymeric material, and an ion exchange polymer, optionally wherein the at least one of the polymeric material, the cross-linked polymeric material, and the ion exchange polymer comprises at least one, and optionally both, of (i) at least 1 wt %, at least 2 wt %, at least 3 wt %, at least 4 wt %, at least 5 wt %, at least 6 wt %, at least 7 wt %, at least 8 wt %, at least 9 wt %, or at least 10 wt % of the bioremediation formulation and (ii) less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, or less than 5 wt % of the bioremediation formulation, and further optionally wherein the wt % includes a wt % of the active components of the bioremediation formulation.

I4. The bioremediation formulation of paragraph I3, wherein the polymeric material includes a naturally occurring polymeric material, and optionally wherein the polymeric material includes at least one of cellulose and hemicellulose.

I5. The bioremediation formulation of any of paragraphs I3-I4, wherein the polymeric material includes a synthetic polymeric material, and optionally wherein the synthetic polymeric material is synthesized from at least one of a styrene monomer, an acrylonitrile monomer, an acrylate ester monomer, and a methacrylate ester monomer.

I6. The bioremediation formulation of any of paragraphs I3-I5, wherein the polymeric material is functionalized with at least one of an electron-withdrawing group, an acid group, and sulfonic acid.

I7. The bioremediation formulation of any of paragraphs I1-I6, wherein the ion exchange resin includes a gel.

I8. The bioremediation formulation of any of paragraphs I1-I7, wherein the ion exchange resin includes a macroreticular structure.

I9. The bioremediation formulation of any of paragraphs I1-I8, wherein the ion exchange resin is formed into at least one of a bead, a sheet, and a powder.

I10. The bioremediation formulation of any of paragraphs I1-I9, wherein the ion exchange resin is a water-soluble ion exchange resin.

I11. The bioremediation formulation of any of paragraphs I1-I10, wherein the bioremediation formulation further includes a cyclic ring hydrocarbon with a cationic functional group, optionally wherein the cyclic ring hydrocarbon includes naphthalene, and further optionally wherein the cationic functional group includes at least one of a mineral acid and sulfonic acid.

I12. The bioremediation formulation of any of paragraphs I1-I11, wherein the bioremediation formulation further includes an acidulating agent, optionally wherein the acidulating agent includes at least one of a mineral acid, sulfuric acid, buffered sulfuric acid, and hydrochloric acid, optionally wherein the acidulating agent comprises at least one, and optionally both, of (i) at least 60 wt %, at least 65 wt %, at least 70 wt %, at least 75 wt %, at least 80 wt %, or at least 85 wt % of the bioremediation formulation and (ii) less than 90 wt %, less than 85 wt %, less than 80 wt %, less than 75 wt %, less than 70 wt %, or less than 65 wt % of the bioremediation formulation, and further optionally wherein the wt % includes a wt % of the active components of the bioremediation formulation.

I13. The bioremediation formulation of any of paragraphs I1-I12, wherein the bioremediation formulation further includes a surfactant, optionally wherein the surfactant includes a sulfonated surfactant, optionally wherein the surfactant comprises at least one, and optionally both, of (i) at least 1 wt %, at least 2 wt %, at least 3 wt %, at least 4 wt %, at least 5 wt %, at least 6 wt %, at least 7 wt %, at least 8 wt %, at least 9 wt %, or at least 10 wt % of the bioremediation formulation and (ii) less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, or less than 5 wt % of the bioremediation formulation, and further optionally wherein the wt % includes a wt % of the active components of the bioremediation formulation.

I14. The bioremediation formulation of any of paragraphs I1-I13, wherein the bioremediation formulation further includes an enzyme, optionally wherein the enzyme comprises at least one, and optionally both, of (i) at least 1 wt %, at least 2 wt %, at least 4 wt %, at least 6 wt %, at least 8 wt %, at least 10 wt %, at least 12 wt %, at least 14 wt %, at least 16 wt %, at least 18 wt % or at least 20 wt % of the bioremediation formulation and (ii) less than 30 wt %, less than 28 wt %, less than 26 wt %, less than 24 wt %, less than 22 wt %, less than 20 wt %, less than 18 wt %, less than 16 wt %, less than 14 wt %, less than 12 wt %, or less than 10 wt % of the bioremediation formulation, and further optionally wherein the wt % includes a wt % of the active components of the bioremediation formulation.

I15. The bioremediation formulation of any of paragraphs I1-I14, wherein the bioremediation formulation further includes a ligno sulfate, optionally wherein the ligno sulfate comprises at least one, and optionally both, of (i) at least 1 wt %, at least 2 wt %, at least 4 wt %, at least 6 wt %, at least 8 wt %, at least 10 wt %, at least 12 wt %, at least 14 wt %, at least 16 wt %, at least 18 wt % or at least 20 wt % of the bioremediation formulation and (ii) less than 30 wt %, less than 28 wt %, less than 26 wt %, less than 24 wt %, less than 22 wt %, less than 20 wt %, less than 18 wt %, less than 16 wt %, less than 14 wt %, less than 12 wt %, or less than 10 wt % of the bioremediation formulation, and further optionally wherein the wt % includes a wt % of the active components of the bioremediation formulation.

I16. The bioremediation formulation of any of paragraphs I1-I15, wherein the bioremediation formulation further includes a binding agent, optionally wherein the binding agent comprises at least one, and optionally both, of (i) at least 1 wt %, at least 2 wt %, at least 4 wt %, at least 6 wt %, at least 8 wt %, at least 10 wt %, at least 12 wt %, at least 14 wt %, at least 16 wt %, at least 18 wt % or at least 20 wt % of the bioremediation formulation and (ii) less than 30 wt %, less than 28 wt %, less than 26 wt %, less than 24 wt %, less than 22 wt %, less than 20 wt %, less than 18 wt %, less than 16 wt %, less than 14 wt %, less than 12 wt %, or less than 10 wt % of the bioremediation formulation, and further optionally wherein the wt % includes a wt % of the active components of the bioremediation formulation.

I17. The bioremediation formulation of any of paragraphs I1-I16, wherein the bioremediation formulation further includes a colloidal dispersant, optionally wherein the colloidal dispersant comprises at least one, and optionally both, of (i) at least 1 wt %, at least 2 wt %, at least 3 wt %, at least 4 wt %, at least 5 wt %, at least 6 wt %, at least 7 wt %, at least 8 wt %, at least 9 wt %, or at least 10 wt % of the bioremediation formulation and (ii) less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, or less than 5 wt % of the bioremediation formulation, and further optionally wherein the wt % includes a wt % of the active components of the bioremediation formulation.

J1. An aqueous bioremediation solution, the solution comprising:
water; and
the bioremediation formulation of any of paragraphs I1-I17.

J2. The aqueous bioremediation solution of paragraph J1, wherein the bioremediation formulation comprises at least one, and optionally both, of (i) at least 0.01 wt %, at least 0.02 wt %, at least 0.04 wt %, at least 0.05 wt %, at least 0.06 wt %, at least 0.08 wt %, at least 0.1 wt %, at least 0.2 wt %, at least 0.3 wt %, at least 0.4 wt %, at least 0.6 wt %, at least 0.8 wt %, at least 1 wt %, at least 2 wt %, at least 4 wt %, at least 6 wt %, at least 8 wt %, at least 9 wt %, at least 10 wt %, at least 20 wt %, at least 30 wt %, at least 40 wt %, or at least 50 wt % of the aqueous bioremediation formulation and (ii) less than 60 wt %, less than 50 wt %, less than 40 wt %, less than 30 wt %, less than 20 wt %, less than 10 wt %, less than 9 wt %, less than 8 wt %, less than 6 wt %, less than 4 wt %, less than 2 wt %, less than 1 wt %, less than 0.8 wt %, less than 0.6 wt %, less than 0.4 wt %, less than 0.3 wt %, less than 0.2 wt %, or less than 0.1 wt % of the aqueous bioremediation formulation.

K1. An aquifer comprising:
  water;
  a contaminant;
  a first bioremediation formulation, wherein the first bioremediation formulation includes the bioremediation formulation of any of paragraphs I1-I17; and
  a second bioremediation formulation, wherein the second bioremediation formulation includes the bioremediation formulation of any of paragraphs A1-D4.

K2. The aquifer of paragraph K1, wherein the contaminant includes a hydrocarbon.

L1. A soil sample comprising:
  soil;
  a contaminant;
  a first bioremediation formulation, wherein the first bioremediation formulation includes the bioremediation formulation of any of paragraphs I1-I17; and
  a second bioremediation formulation, wherein the second bioremediation formulation includes the bioremediation formulation of any of paragraphs A1-D4.

L2. The soil sample of paragraph L1, wherein the contaminant includes a hydrocarbon.

M1. A kit of bioremediation formulations to be utilized during the bioremediation of a contaminated region, the kit comprising:
  a first bioremediation formulation that is configured to be supplied to a first treatment zone that is associated with the contaminated region, wherein the first bioremediation formulation includes the bioremediation formulation of any of paragraphs I1-I17; and
  a second bioremediation formulation that is configured to be supplied to a second treatment zone that is associated with the contaminated region after the first bioremediation formulation has been supplied to the first treatment zone, wherein the second bioremediation formulation includes the bioremediation formulation of any of paragraphs A1-D4, and optionally wherein the first bioremediation formulation and the second bioremediation formulation are configured to be supplied to the first treatment zone and the second treatment zone, respectively, using the method of any of paragraphs N1-N48.

N1. A method of decreasing a concentration of a contaminant contained within a contaminated region, the method comprising:
  supplying a first bioremediation formulation to a first treatment zone that is associated with the contaminated region; and
  supplying a second bioremediation formulation to a second treatment zone that is associated with the contaminated region.

N2. The method of paragraph N1, wherein the supplying the first bioremediation formulation includes supplying one of (i) the bioremediation formulation of any of paragraphs I1-I17 and (ii) the aqueous bioremediation solution of any of paragraphs J142.

N3. The method of any of paragraphs N1-N2, wherein supplying the second bioremediation formulation includes supplying one of (i) the bioremediation formulation of any of paragraphs A1-D4 and (ii) the aqueous bioremediation solution of any of paragraphs E1-E2, and optionally wherein supplying the second bioremediation formulation includes supplying the second bioremediation formulation immediately after supplying the first bioremediation formulation.

N4. The method of any of paragraphs N1-N3, wherein, subsequent to supplying the first bioremediation formulation, the method further includes waiting for a treatment time prior to supplying the second bioremediation formulation.

N5. The method of paragraph N4, wherein the treatment time includes a treatment time of at least one, and optionally both, of (i) at least 1 hour (h), at least 2 h, at least 4 h, at least 6 h, at least 8 h, at least 10 h, at least 12 h, at least 16 h, at least 20 h, at least 1 day, at least 2 days, at least 3 days, at least 4 days, at least 5 days, at least 6 days, at least 8 days, at least 10 days, at least 12 days, at least 14 days, at least 16 days, at least 20 days, at least 25 days, at least 30 days, at least 40 days, at least 50 days, at least 60 days, at least 70 days, at least 80 days, or at least 90 days and (ii) less than 100 days, less than 90 days, less than 80 days, less than 70 days, less than 60 days, less than 50 days, less than 40 days, less than 30 days, less than 25 days, less than 20 days, less than 16 days, less than 14 days, less than 12 days, less than 10 days, less than 8 days, less than 6 days, less than 5 days, less than 4 days, less than 3 days, less than 2 days, less than 1 day, less than 20 h, less than 16 h, less than 12 h, less than 10 h, less than 8 h, less than 6 h, less than 4 h, less than 2 h, or less than 1 h.

N6. The method of any of paragraphs N1-N5, wherein the second treatment zone is at least partially coextensive, and optionally is coextensive, with the first treatment zone.

N7. The method of any of paragraphs N1-N6, wherein the supplying the second bioremediation formulation to the second treatment zone includes supplying the second bioremediation formulation to a zone that is at least partially coextensive, and optionally is coextensive, with the first treatment zone.

N8. The method of any of paragraphs N1-N7, wherein the second treatment zone is contained within the first treatment zone.

N9. The method of any of paragraphs N1-N7, wherein the second treatment zone extends outside of the first treatment zone.

N10. The method of any of paragraphs N1-N9, wherein the contaminated region includes a subsurface region, and optionally wherein the method includes supplying the first bioremediation formulation and supplying the second bioremediation formulation to the subsurface region.

N11. The method of paragraph N10, wherein at least one, and optionally both, of the supplying the first bioremediation formulation and the supplying the second bioremediation formulation includes supplying through at least one of a borehole and a groundwater well that extends between a surface region and the subsurface region.

N12. The method of any of paragraphs N10-N11, wherein at least one, and optionally both, of the supplying the first bioremediation formulation and the supplying the second bioremediation formulation includes supplying through at least one of a horizontal slotted pipe, a shallow well, and a vapor extraction well, and optionally wherein the supplying includes supplying to a vadose zone of the subsurface region.

N13. The method of any of paragraphs N1-N9, wherein the contaminated region includes a soil sample that has been removed from a contaminated site, and optionally wherein the method includes supplying the first bioremediation formulation and supplying the second bioremediation formulation to the soil sample.

N14. The method of any of paragraphs N1-N13, wherein the method further includes supplying bacteria to the contaminated region, optionally wherein the supplying bacteria is performed separately from the supplying the first bioremediation formulation and the supplying the second bioremediation formulation, optionally wherein the supplying bacteria is performed subsequent to the supplying the first bioremediation formulation and prior to the supplying the second bioremediation formulation, optionally wherein the supplying bacteria is performed subsequent to the supplying the first bioremediation formulation and subsequent to the supplying the second bioremediation formulation, and further optionally wherein the supplying bacteria includes supplying at least one of a *pseudomonas* species of bacteria and a *bacillus* species of bacteria.

N15. The method of any of paragraphs N1-N14, wherein the method further includes supplying a surfactant to the contaminated region, and optionally wherein the supplying a surfactant includes at least one of supplying the surfactant concurrently with the supplying the second bioremediation formulation and mixing the surfactant with the second bioremediation formulation prior to the supplying the second bioremediation formulation.

N16. The method of any of paragraphs N1-N14, wherein at least one, and optionally both, of the supplying a first bioremediation formulation and the supplying a second bioremediation formulation includes supplying at a supply pressure, and optionally wherein the supply pressure includes a supply pressure of at least one, and optionally both, of (i) at least 10 kilopascals (kPa), at least 20 kPa, at least 30 kPa, at least 40 kPa, at least 50 kPa, at least 60 kPa, at least 70 kPa, at least 80 kPa, at least 90 kPa, at least 100 kPa, at least 150 kPa, at least 200 kPa, at least 250 kPa, at least 300 kPa, at least 500 kPa, at least 750 kPa, at least 1 megapascal (MPa), at least 2 MPa, at least 4 MPa, at least 6 MPa, at least 8 MPa, at least 10 MPa, or at least 15 MPa and (ii) less than 25 MPa, less than 20 MPa, less than 15 MPa, less than 10 MPa, less than 8 MPa, less than 6 MPa, less than 4 MPa, less than 2 MPa, less than 1 MPa, less than 750 kPa, less than 500 kPa, less than 300 kPa, less than 250 kPa, less than 200 kPa, less than 150 kPa, or less than 100 kPa.

N17. The method of any of paragraphs N1-N16, wherein the method further includes repeating the method.

N18. The method of paragraph N17, wherein the repeating includes periodically supplying the first bioremediation formulation and subsequently supplying the second bioremediation formulation after each periodic supply of the first bioremediation formulation.

N19. The method of any of paragraphs N1-N18, wherein the method includes supplying the first bioremediation formulation prior to supplying the second bioremediation formulation.

N20. The method of any of paragraphs N1-N19, wherein the contaminated region includes a/the subsurface region that includes the contaminant, optionally wherein the contaminant is located in at least one, optionally at least two, and further optionally all of a/the vadose zone of the subsurface region, a smear zone of the subsurface region, and a saturated zone of the subsurface region, and further optionally wherein at least one of the first treatment zone and the second treatment zone includes at least one of the vadose zone, the smear zone, and the saturated zone.

N21. The method of paragraph N20, wherein a/the borehole extends from a/the surface region and within the contaminated region, and further wherein the supplying the first bioremediation formulation and the supplying the second bioremediation formulation includes supplying both the first bioremediation formulation and the second bioremediation formulation from the surface region and to the contaminated region through the borehole.

N22. The method of paragraph N21, wherein the supplying the first bioremediation formulation and the supplying the second bioremediation formulation includes supplying at a/the supply pressure of 300 kPa to 20 MPa.

N23. The method of any of paragraphs N21-N22, wherein the method further includes forming the borehole, optionally wherein the forming the borehole includes forming the borehole with at least one of a high pressure lance, a water knife, and a push probe.

N24. The method of any of paragraphs N21-N23, wherein the supplying the first bioremediation formulation includes supplying a dilute aqueous solution of the first bioremediation formulation, optionally wherein the dilute aqueous solution of the first bioremediation formulation includes the aqueous bioremediation solution of any of paragraphs J1-J2, optionally wherein the first bioremediation formulation comprises 0.03-0.3 wt % of the dilute aqueous solution of the first bioremediation formulation, and further optionally wherein the first bioremediation formulation is diluted in at least one of municipal tap water, ground water, and surface water to form the dilute aqueous solution of the first bioremediation formulation.

N25. The method of paragraph N24, wherein supplying the dilute aqueous solution of the first bioremediation formulation includes injecting the dilute aqueous solution of the first bioremediation formulation along a portion of a length of the borehole, and optionally includes injecting at least one, and optionally both, of (i) at least 1 liter (L), at least 2 L, at least 3 L, at least 4 L, at least 5 L, at least 6 L, at least 8 L, at least 10 L, or at least 12 L of the dilute aqueous solution of the first bioremediation formulation per meter of the portion of the length of the borehole and (ii) less than 15 L, less than 14 L, less than 12 L, less than 10 L, less than 8 L, less than 6 L, less than 5 L, less than 4 L, less than 3 L, or less than 2 L of the dilute aqueous solution of the first bioremediation formulation per meter of the portion of the length of the borehole.

N26. The method of any of paragraphs N21-N25, wherein supplying the second bioremediation formulation includes supplying an aqueous solution of the second bioremediation formulation, optionally wherein the aqueous solution of the second bioremediation formulation includes the aqueous bioremediation solution of any of paragraphs E1-E2, and further optionally wherein the method further includes mechanically mixing a portion of the contaminated region to distribute the second bioremediation formulation within the portion of the contaminated region.

N27. The method of paragraph N26, wherein supplying the aqueous solution of the second bioremediation formulation includes injecting the aqueous solution of the second bioremediation formulation along a/the portion of a/the length of the borehole, and optionally includes injecting at least one, and optionally both, of (i) at least 1 kilogram (kg), at least 2 kg, at least 3 kg, at least 4 kg, at least 5 kg, at least 6 kg, at least 8 kg, at least 10 kg, at least 12 kg, at least 14 kg, at least 16 kg, at least 18 kg, at least 20 kg, at least 22 kg, at least 24 kg, at least 26 kg, or at least 28 kg of the second bioremediation formulation per meter of the portion of the length of the borehole and (ii) less than 30 kg, less than 28 kg, less than 26 kg, less than 24 kg, less than 22 kg, less than 20 kg, less than 18 kg, less than 16 kg, less than 14 kg, less than 12 kg, less than 10 kg, less than 8 kg, less than 6 kg, less than 4 kg, or less than 2 kg of the second bioremediation formulation per meter of the portion of the length of the borehole.

N28. The method of any of paragraphs N21-N27, wherein the supplying the second bioremediation formulation includes supplying the second bioremediation formulation using the method of any of paragraphs H1-H18.

N29. The method of any of paragraphs N21-N28, wherein the supplying the first bioremediation formulation includes supplying the first bioremediation formulation to a portion of the subsurface region that extends between the surface region and a total treatment depth, and optionally wherein the total treatment depth is within one of the saturated zone and the vadose zone.

N30. The method of any of paragraphs N21-N29, wherein the supplying the second bioremediation formulation includes supplying the second bioremediation formulation to a portion of the subsurface region that extends between one of (i) the smear zone and a/the total treatment depth, (ii) the surface region and the total treatment depth, and (iii) the smear zone and the saturated zone.

N31. The method of any of paragraphs N21-N30, wherein, subsequent to the supplying the first bioremediation formulation and the supplying the second bioremediation formulation, the method further includes backfilling the borehole, optionally wherein the backfilling includes backfilling with at least one of bentonite and concrete.

N32. The method of any of paragraphs N21-N31, wherein the borehole is a first borehole, and further wherein the method includes repeating the method in a second borehole.

N33. The method of paragraph N32, wherein the method further includes repeating the method a plurality of times in a plurality of boreholes, wherein the method includes creating the plurality of boreholes, and further wherein at least one of a number of boreholes in the plurality of boreholes and a spacing among the plurality of boreholes is based, at least in part, on at least one of a total mass of contaminant within the contaminated region and an extent of the contaminated region.

N34. The method of any of paragraphs N21-N31, wherein the method further includes fluidly isolating at least a portion of a/the borehole from a remainder of the borehole, optionally wherein the fluidly isolating includes fluidly isolating subsequent to supplying the first bioremediation formulation and prior to supplying the second bioremediation formulation, and further optionally wherein the fluidly isolating includes fluidly isolating with at least one of a packer and hydrated bentonite.

N35. The method of paragraph N20, wherein the supplying the first bioremediation formulation includes supplying a dilute aqueous solution of the first bioremediation formulation to the vadose zone and flowing the dilute aqueous solution of the first bioremediation formulation through the subsurface region to the saturated zone, optionally wherein the dilute aqueous solution of the first bioremediation formulation includes the aqueous bioremediation solution of any of paragraphs J1-J2, optionally wherein the first bioremediation formulation comprises 0.01-0.3 wt % of the dilute aqueous solution of the first bioremediation formulation, and further optionally wherein supplying the dilute aqueous solution of the first bioremediation formulation to the vadose zone includes supplying the dilute aqueous solution of the first bioremediation formulation to an infiltration gallery that includes at least one of a horizontal slotted pipe and a shallow well that is present within the vadose zone.

N36. The method of paragraph N35, wherein the supplying the dilute aqueous solution of the first bioremediation formulation includes saturating a portion of the contaminated region between the vadose zone and the saturated zone with the dilute aqueous solution of the first bioremediation formulation.

N37. The method of any of paragraphs N35-N36, wherein the supplying the second bioremediation formulation includes supplying an aqueous solution of the second bioremediation formulation, and optionally wherein the second bioremediation formulation comprises at least one, and optionally both, of (i) at least 0.01 wt %, at least 0.02 wt %, at least 0.05 wt %, at least 0.1 wt %, at least 0.5 wt %, at least 1 wt %, at least 2.5 wt %, at least 5 wt %, at least 7.5 wt %, or at least 10 wt % of the aqueous solution of the second bioremediation formulation and (ii) less than 15 wt %, less than 12.5 wt %, less than 10 wt %, less than 7.5 wt %, less than 5 wt %, less than 2.5 wt %, less than 1 wt %, or less than 0.5 wt % of the aqueous solution of the second bioremediation formulation.

N38. The method of paragraph N37, wherein the supplying the aqueous solution of the second bioremediation formulation includes saturating a portion of the contaminated region between the vadose zone and the saturated zone with the aqueous solution of the second bioremediation formulation.

N40. The method of paragraph N20, wherein the supplying the first bioremediation formulation includes supplying the first bioremediation formulation to a/the groundwater well that extends between a/the surface region and within the contaminated region, and further wherein the supplying the second bioremediation formulation includes supplying the second bioremediation formulation to the groundwater well.

N41. The method of paragraph N40, wherein the supplying the second bioremediation formulation includes supplying an aqueous solution of the second bioremediation formulation, and optionally wherein the second bioremediation formulation comprises at least one, and optionally both, of (i) at least 0.1 wt %, at least 0.25 wt %, at least 0.5 wt %, at least 1 wt %, at least 2 wt %, at least 3 wt %, at least 4 wt %, at least 5 wt %, at least 6 wt %, at least 8 wt %, at least 10 wt %, at least 15 wt %, or at least 20 wt % of the aqueous solution of the second bioremediation formulation and (ii) less than 30 wt %, less than 25 wt %, less than 20 wt %, less than 15 wt %, less than 10 wt %, less than 8 wt %, less than 7 wt %, less than 6 wt %, less than 5 wt %, less than 4 wt %, less than 3 wt %, less than 2 wt %, or less than 1 wt % of the aqueous solution of the second bioremediation formulation.

N42. The method of any of paragraphs N40-N41, wherein the groundwater well is a first groundwater well, wherein the method further includes producing groundwater from a second groundwater well, wherein the method includes recirculating the groundwater from the second groundwater well to the first groundwater well and injecting the groundwater into the contaminated region with the first groundwater well.

N43. The method of paragraph N42, wherein the supplying the first bioremediation formulation includes mixing the first bioremediation formulation with the groundwater from the second groundwater well prior to the recirculating, and further wherein the supplying the second bioremediation formulation includes mixing the second bioremediation formulation with the groundwater from the second groundwater well prior to the recirculating.

N44. The method of any of paragraphs N40-N43, wherein the supplying the first bioremediation formulation and the supplying the second bioremediation formulation includes periodically supplying the first bioremediation formulation and subsequently supplying the second bioremediation formulation after each periodic supply of the first bioremediation formulation.

N45. The method of any of paragraphs N1-N19, wherein the contaminated region includes a soil sample that has been excavated from a contaminated site.

N46. The method of paragraph N45, wherein the supplying the first bioremediation formulation includes spraying an aqueous solution of the first bioremediation formulation onto the soil sample.

N47. The method of any of paragraphs N45-N46, wherein the method further includes mechanically mixing the second bioremediation formulation with the soil sample.

N48. The method of any of paragraphs N45-N47, wherein the method further includes excavating the soil sample from the contaminated site, optionally wherein the supplying the first bioremediation formulation is performed prior to the excavating, and further optionally wherein the supplying the second bioremediation formulation is performed subsequent to the excavating.

In the present disclosure, several of the illustrative, non-exclusive examples of methods have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently. It is also within the scope of the present disclosure that the blocks, or steps, may be implemented as logic, which also may be described as implementing the blocks, or steps, as logics. In some applications, the blocks, or steps, may represent expressions and/or actions to be performed by functionally equivalent circuits or other logic devices. The illustrated blocks may, but are not required to, represent executable instructions that cause a computer, processor, and/or other logic device to respond, to perform an action, to change states, to generate an output or display, and/or to make decisions.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and define a term in a manner or are otherwise inconsistent with either the non-incorporated portion of the present disclosure or with any of the other incorporated references, the non-incorporated portion of the present disclosure shall control, and the term or incorporated disclosure therein shall only control with respect to the reference in which the term is defined and/or the incorporated disclosure was originally present.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A method of decreasing a concentration of a hydrocarbon contaminant contained within a contaminated region through in situ anaerobic oxidative bioremediation of the hydrocarbon contaminant by native microorganisms that are present within the contaminated region, the method comprising:
   supplying a first bioremediation formulation that includes a cationic ion exchange resin to the contaminated region to promote metabolism of the hydrocarbon contaminant by the native microorganisms via anaerobic microbial respiration; and subsequent to the supplying the first bioremediation formulation, supplying a second bioremediation formulation to the contaminated region to enhance growth of the native microorganisms and to promote metabolism of the hydrocarbon contaminant by the native microorganisms via anaerobic microbial respiration, wherein the second bioremediation formulation includes:
(i) a sulfate salt that comprises 20-40 wt % of the second bioremediation formulation;
(ii) a nitrate salt that comprises 1-50 wt % of the second bioremediation formulation;
(iii) a phosphate salt that comprises 15-25 wt % of the second bioremediation formulation;
(iv) a complex sugar that comprises 3-7 wt % of the second bioremediation formulation; and
(v) Brewer's yeast that comprises 5-10 wt % of the second bioremediation formulation.

2. The method of claim 1, wherein, subsequent to the supplying the first bioremediation formulation, the method further includes waiting for a treatment time of 0.5 to 100 days prior to the supplying the second bioremediation formulation.

3. The method of claim 1, wherein the supplying the first bioremediation formulation includes supplying an aqueous solution of the first bioremediation formulation that comprises 0.01-60 wt % of the first bioremediation formulation in water.

4. The method of claim 1, wherein the supplying the second bioremediation formulation includes supplying 0.5-5 kilograms of the second bioremediation formulation for each kilogram of hydrocarbon contaminant that is contained within the contaminated region.

5. The method of claim 1, wherein the cationic ion exchange resin includes a polymeric material, wherein the supplying the first bioremediation formulation includes supplying the polymeric material.

6. The method of claim 1, wherein the first bioremediation formulation further includes an additional component, wherein the additional component includes at least one of a cyclic ring hydrocarbon with a cationic functional group, an acidulating agent, a surfactant, an enzyme, a ligno sulfate, a binding agent, and a colloidal dispersant, and further wherein the supplying the first bioremediation formulation includes supplying the additional component.

7. The method of claim 1, wherein the supplying the first bioremediation formulation and the supplying the second bioremediation formulation includes supplying both the first bioremediation formulation and the second bioremediation formulation to a single application site that includes at least one of a borehole, a groundwater well, and an infiltration gallery.

8. The method of claim 1, wherein the method further includes supplying bacteria to the contaminated region subsequent to the supplying the first bioremediation formulation and subsequent to the supplying the second bioremediation formulation.

9. The method of claim 1, wherein the method further includes supplying a surfactant to the contaminated region.

10. The method of claim 1, wherein the contaminated region includes a subsurface region, and further wherein the method includes supplying the first bioremediation formulation to the subsurface region and supplying the second bioremediation formulation to the subsurface region.

11. The method of claim 1, wherein the contaminated region includes a subsurface region, and wherein the supplying the first bioremediation formulation includes supplying the first bioremediation formulation to the subsurface region in situ, and further wherein the supplying the second bioremediation formulation includes supplying the second bioremediation formulation to the subsurface region in situ.

12. The method of claim 1, wherein the method includes supplying the second bioremediation formulation such that the second bioremediation formulation is at least partially coextensive with the first bioremediation formulation within the contaminated region.

13. The method of claim 1, wherein the contaminated region is located within a vadose zone, wherein the supplying the first bioremediation formulation includes supplying the first bioremediation formulation to the vadose zone, and further wherein the supplying the second bioremediation formulation includes supplying the second bioremediation formulation to the vadose zone.

14. The method of claim 1, wherein the contaminated region is located within a smear zone, wherein the supplying the first bioremediation formulation includes supplying the first bioremediation formulation to the smear zone, and further wherein the supplying the second bioremediation formulation includes supplying the second bioremediation formulation to the smear zone.

15. The method of claim 2, wherein the waiting includes waiting to permit the first bioremediation formulation to react with the hydrocarbon contaminant prior to the supplying the second bioremediation formulation.

\* \* \* \* \*